United States Patent
Yamashita et al.

(10) Patent No.: US 12,275,652 B2
(45) Date of Patent: Apr. 15, 2025

(54) WATER QUALITY MANAGEMENT METHOD, ION ADSORPTION DEVICE, INFORMATION PROCESSING DEVICE AND INFORMATION PROCESSING SYSTEM

(71) Applicant: ORGANO CORPORATION, Tokyo (JP)

(72) Inventors: Yukinari Yamashita, Tokyo (JP); Daisaku Yano, Tokyo (JP); Kyohei Tsutano, Tokyo (JP)

(73) Assignee: ORGANO CORPORATION, Tokyo (JP)

( * ) Notice: Subject to any disclaimer, the term of this patent is extended or adjusted under 35 U.S.C. 154(b) by 933 days.

(21) Appl. No.: 17/285,671

(22) PCT Filed: Oct. 17, 2019

(86) PCT No.: PCT/JP2019/040870
§ 371 (c)(1),
(2) Date: Apr. 15, 2021

(87) PCT Pub. No.: WO2020/080461
PCT Pub. Date: Apr. 23, 2020

(65) Prior Publication Data
US 2021/0395106 A1  Dec. 23, 2021

(30) Foreign Application Priority Data
Oct. 17, 2018 (JP) .................. 2018-195690

(51) Int. Cl.
*C02F 1/00* (2023.01)
*C02F 1/42* (2023.01)
(Continued)

(52) U.S. Cl.
CPC ............. *C02F 1/008* (2013.01); *C02F 1/42* (2013.01); *G01N 1/20* (2013.01); *G01N 33/18* (2013.01);
(Continued)

(58) Field of Classification Search
CPC ........ G01N 1/20; G01N 33/18; G01N 1/2035; G01N 2001/205; G01N 2001/2826;
(Continued)

(56) References Cited

U.S. PATENT DOCUMENTS 4,786,473 A * 11/1988 Mukogawa ............ G01N 15/06
73/61.73
2014/0183025 A1 * 7/2014 Kamen ................. B01D 1/2896
202/185.1
(Continued)

FOREIGN PATENT DOCUMENTS

CN  107158747 A  9/2017
JP  5-45351 A  2/1993
(Continued)

OTHER PUBLICATIONS

International Search Report issued in International Patent Application No. PCT/JP2019/040870, dated Jan. 7, 2020, along with English translation thereof.
(Continued)

*Primary Examiner* — John Fitzgerald
*Assistant Examiner* — Truong D Phan
(74) *Attorney, Agent, or Firm* — GREENBLUM & BERNSTEIN, P.L.C.

(57) ABSTRACT

A water quality management method for managing the concentration of impurity ions contained in the water to be analyzed includes connecting the ion adsorption device in which the ion adsorbent and the accumulated flow rate meter are provided to the branch pipe, passing the water being
(Continued)

analyzed from the branch pipe to the ion adsorbent for a predetermined period of time to the ion adsorption device and adsorbing ions contained in the water being analyzed an ion adsorbent sample. In the ion adsorption device, an accumulated flow rate meter is provided on the downstream side of the flow direction of the water being analyzed of the ion adsorbent.

15 Claims, 15 Drawing Sheets

(51) Int. Cl.
*C02F 101/10* (2006.01)
*C02F 103/04* (2006.01)
*G01N 1/20* (2006.01)
*G01N 33/18* (2006.01)

(52) U.S. Cl.
CPC ...... *C02F 2101/10* (2013.01); *C02F 2103/04* (2013.01); *C02F 2201/005* (2013.01); *C02F 2209/003* (2013.01); *C02F 2209/40* (2013.01)

(58) Field of Classification Search
CPC .... G01N 1/405; G01N 5/02; G01N 2021/495; G01N 30/00; G01N 2291/0256; G01N 1/38; G01N 1/14; C02F 1/008; C02F 1/42; C02F 2103/04; C02F 2209/40; C02F 1/20; C02F 1/28; C02F 1/32; C02F 1/444; C02F 2101/10; C02F 2101/20; C02F 2201/005; C02F 2209/003; C02F 9/00
See application file for complete search history.

(56) References Cited

U.S. PATENT DOCUMENTS

| 2014/0229414 | A1* | 8/2014 | Goldberg | G06N 5/04 706/46 |
| 2016/0334311 | A1* | 11/2016 | Westerhoff | G01N 1/405 |

FOREIGN PATENT DOCUMENTS

| JP | 5-59237 U | 8/1993 |
| JP | 2001-056333 A | 2/2001 |
| JP | 2001-153854 A | 6/2001 |
| JP | 2004169746 A * | 6/2004 |
| JP | 2009-156692 A | 7/2009 |
| JP | 2011-113425 A | 6/2011 |
| JP | 2012-93217 A | 5/2012 |
| JP | 2012-205996 A | 10/2012 |
| JP | 2016-221427 A | 12/2016 |
| JP | 2017-227577 A | 12/2017 |
| KR | 10-2013-0123737 | 11/2013 |

OTHER PUBLICATIONS

Written Opinion of the International Searching Authority issued in International Patent Application No. PCT/JP2019/040870, dated Jan. 7, 2020, along with English translation thereof.
Office Action issued Sep. 6, 2023 in family member Taiwanese application No. 108137467 with English translation thereof.
Office Action issued in corresponding Chinese Patent Application No. 201980064439.1 dated Sep. 16, 2022, along with partial English machine translation thereof; category indications (X, Y, etc. not translated as they are self-evident).
Office Action issued in corresponding Korean Patent Application No. 10-2021-7013615 dated Sep. 30, 2022, along with English machine translation thereof.

* cited by examiner

FIG.7

| Customer No. | System No. | Device No. | Adsorbent information |
|---|---|---|---|
| A001 | 1 | 1 | A001-1-1 |
| | | 2 | A001-1-2 |
| | 2 | 1 | A001-2-1 |
| | | 2 | A001-2-2 |
| B002 | 1 | 1 | B002-1-1 |
| | | 2 | B002-1-2 |
| | | 3 | B002-1-3 |
| | 2 | 1 | B002-2-1 |
| | | 2 | B002-2-2 |
| ⋮ | ⋮ | ⋮ | ⋮ |

FIG.8

| Period | 2019/5/1~<br>2019/5/5 | 2019/5/6~<br>2019/5/10 | 2019/5/11~<br>2019/5/15 | 2019/5/16~<br>2019/5/20 | ... |
|---|---|---|---|---|---|
| Flow rate[L] | 1000 | 980 | 1000 | 990 | ... |
| Adsorbent No. | A00010001 | A00020001 | A00030001 | A00040001 | ... |

WATER QUALITY MANAGEMENT METHOD, ION ADSORPTION DEVICE, INFORMATION PROCESSING DEVICE AND INFORMATION PROCESSING SYSTEM

TECHNICAL FIELD

The present invention relates to a water quality management method for managing an impurity concentration in ultrapure water, and more particularly, to a water quality management method for quantifying ultra-trace metal impurities in ultrapure water, an ion adsorption device and an information processing apparatus used in the water quality management method, and an information processing system using the same.

BACKGROUND ART

Ultrapure water is generally produced by treating water to be treated such as river water, groundwater and industrial water in a pretreatment step to remove most of suspended matter and organic matter in the water to be treated, and then the pretreated water is sequentially treated with a primary system pure water producing apparatus and a secondary system pure water producing apparatus (subsystem). Produced ultrapure water, for example in a semiconductor device manufacturing factory, is supplied to the point of use where wafer cleaning or the like will be performed. Ultrapure water is also widely used in pharmaceutical manufacturing processes, etc. Although the terms "pure water" and "ultrapure water" are not generally clearly defined, in this specification, high-purity water that is described in terms of "pure water", "ultrapure water", and the like will be generically referred to as "ultrapure water"

Ultrapure water has such high purity that the quantitation of impurities contained therein is also difficult, but does not contain any impurities at all. The effect of ultra-trace components contained in ultrapure water on products such as semiconductor devices becomes non-negligible as the degree of integration in the device increases. For this reason, the need for ultrapure water having even higher purity than conventional ultrapure water has also been studied.

Ultrapure water produced by subsystems in semiconductor device manufacturing factories, etc. is supplied to the point of use through pipe, but the pipe length between the subsystem and the point of use may extend to several hundred meters when it is long. Therefore, impurities such as fine particles and metal ion components from the pipe are mixed into the ultrapure water, and although slight, may adversely affect the characteristics of the semiconductor device to be manufactured. As an example, metal impurities in ultrapure water may deteriorate the electrical characteristics of the device, the particles may cause defects such as pattern defects and disconnection, dielectric strength reduction. Further, if a component that has not been removed in an ultrapure water production apparatus or a leak of impurities occurs instantaneously or over a period of time for some reason from an ultrapure water production apparatus, the characteristics of the device to be manufactured may be adversely affected as well. Therefore, it is extremely important to manage the water quality of ultrapure water supplied to the point of use.

Water quality analysis items for ultrapure water include resistivity (or its reciprocal conductivity), particulate count, viable count, and further concentrations of items such as TOC (Total Organic Carbon; total organic carbon), dissolved oxygen (DO), hydrogen peroxide, silica, cationic ions, anionic ions, and heavy metals. Regarding resistivity, number of fine particles, TOC, dissolved oxygen, etc., instruments for on-line measurement are used. Ionic impurities are also measured on-line by a measurement instrument. If the concentration is below the lower detection limit of the on-line measuring instrument, it is necessary to quantify after concentrating the impurities by some method. Metal ions need to be quantified, for example, on the order of 0.01 ppt. However, the current analytical method cannot be used for the quantitation unless the concentration of impurities in ultrapure water is carried out. One of the methods for concentrating and quantifying impurities is a method in which water being analyzed is distilled and concentrated by a special device in a clean room, and then normal quantitation is performed (distillation method). However, in the distillation method, since the ionic impurity concentration becomes lower, the amount of water being analyzed and being evaporated increases, and the operation becomes complicated, so that there is a high possibility that contamination occurs. In addition, in the case of an element having volatility, a correct quantitative result may not be obtained in some cases.

As another method of concentrating and quantifying impurities, there is a method (concentration method) in which water being analyzed is passed through an ion exchanger such as a porous membrane or an ion exchange resin having an ion exchange function, and then the ion exchanger is collected and the captured ionic impurities are eluted by an eluent, and the ionic impurities that are transferred to the eluent are quantified. Patent Document 1 discloses an analysis method for analyzing a concentration method using a porous membrane having an ion exchange function. In addition, Patent Document 2 discloses an impurity concentration monitoring method for quantifying an ionic impurity concentration in water being analyzed in a period of time by repeating the passing the water being analyzed over a predetermined period of time into a porous membrane having an ion exchange function in order to continuously monitor the concentration of an extremely trace amount of ionic impurities in ultrapure water, and quantifying the ionic impurities captured in the porous membrane at each period of time.

As yet another method for concentrating ionic impurities in ultrapure water, Patent Document 3 proposes a method in which a pH of water being analyzed is adjusted to be acidic, and then water being analyzed is supplied to a reverse osmosis (RO) membrane, and a metal ion contained in the concentrated water of the reverse osmosis membrane, that is, water that has not passed through the reverse osmosis membrane is continuously monitored. However, in the method disclosed in Patent Document 3, since the concentration rate of ionic impurities is not so high when using a reverse osmosis membrane, it is not possible to realize the quantitation of impurity metals on the order of 0.01 ppt in the water being analyzed, and it is not possible to satisfy the demand currently required for water quality management of ultrapure water.

PRIOR ART DOCUMENTS

Patent Document

[Patent Document 1] JPH5-45351A
[Patent Document 2] JP2001-153854A
[Patent Document 3] JP2009-156692A

SUMMARY OF INVENTION

Technical Problem

As a method for quantifying ultra-trace amounts of ionic impurities in ultrapure water, the concentration method has a small fear of contamination without a requiring complicated operation, and it is also possible to quantify an element which is easily volatilized. Such analytical techniques have been improved for the purpose of the quantitation of ultra-trace amounts of impurities contained in ultrapure water and play an important role in determining whether the water quality of ultrapure water meets its specifications immediately after completion of the ultrapure water production equipment or after maintenance. However, in the impurity concentration monitoring method described in Patent Document 2, when the flow rate of the water being analyzed that is flowing through the porous membrane by such pressure fluctuations in the pipe system for delivering the water being analyzed is changed, the impurity concentration of the water being analyzed is not calculated, by taking into account the change and, as a result, the quantitative accuracy is reduced.

Incidentally, when it is discovered that a defect or the like has occurred in a product manufactured through a step of using ultrapure water, an analysis is carried out by collecting a sample from the ultrapure water used, the possibility that the water quality of ultrapure water has deteriorated as a part of the defect analysis should be taken into account. In this case, even if pollutants contained in ultrapure water are the cause of the defect, it is common for a considerable amount of time to have passed since the event causing the defect occurred, until sampling, so that at the survey stage, the pollutants were not already present in the ultrapure water, and even though much time and labor was spent investigating the cause, the cause was sometimes unclear.

It is an object of the present invention to provide a water quality management method which can perform an accurate quantitation of an extremely trace amount of ionic impurities in an analysis target water later and which can facilitate the implementation of a defect analysis, an ion adsorption device and an information processing apparatus used in the water quality management method, and an information processing system using the same.

Solution to Problem

The water quality management method of the present invention includes a water quality management method for managing the concentration of impurity ions contained in the water being analyzed, comprising processing for connecting an ion adsorption device in which an ion adsorbent and an accumulated flow rate meter are provided to a branch pipe through which the water being analyzed flows, and processing for passing the water being analyzed from the branch pipe to the ion adsorbent for a predetermined period of time with respect to the ion adsorption device, and adsorbing ions contained in the water being analyzed to an ion adsorbent sample, wherein the accumulated flow rate meter in the ion adsorption device is provided on the downstream side of the flow direction of water being analyzed of the ion adsorbent.

The ion adsorption device of the present invention is characterized in that, an ion adsorption device which is detachably connected to a branch pipe through which water being analyzed flows, comprising an ion adsorbent that is provided removably and that adsorbs ions of the water being analyzed through which the water being analyzed is passed, an accumulated flow rate meter that is provided on a downstream side of a flow direction of the water being analyzed, of the ion adsorbent, and that measures the accumulated value of the water flow rate of the ion adsorbent, and a first valve that is disposed between the ion adsorbent and the accumulated flow rate meter, performs conduction and shutting off the water to be analyzed, and is capable of adjusting the flow rate of the being be analyzed.

The information processing apparatus of the present invention, comprising an input unit that inputs input information based on an operation received from outside, a database that stores period information indicating a time when an ion adsorbent for adsorbing ions of the water being analyzed through which the water being analyzed is passed is attached to a branch pipe through which the water being analyzed is passed and the adsorbent identification information assigned to the ion adsorbent specific in association with each other, a retrieval unit that retrieves the adsorbent identification information from the database based on the date and time information included in the input information input by the input unit, and an output unit that outputs the adsorbent identification information retrieved by the retrieval unit.

The information processing system of the present invention, comprising an ion adsorption device, a quantitation apparatus, and an information processing apparatus, wherein the ion adsorption device, comprises:

an ion adsorbent that is removably provided in a branch pipe in which the water being analyzed flows, and that adsorbs ions of the water being analyzed through which the water being analyzed is passed, and an accumulated flow rate meter that is provided on the downstream side of the flow direction of the water being analyzed of the ion adsorbent, and that measures the accumulated value of the water flow rate of the ion adsorbent, wherein the quantitation apparatus performs quantitative analysis on the ion adsorbent which ion has been adsorbed using the accumulated value which the accumulated flow rate meter has measured, wherein the information processing apparatus, comprises:

an input unit that inputs input information based on an operation received from outside, a database that stores period information indicating the time when the ion adsorbent has been attached to the branch pipe and the adsorbent identification information assigned to the ion adsorbent specific in association with each other, a retrieval unit that retrieves the adsorbent identification information from the database based on the date and time information included in the input information input by the input unit, and an output unit that outputs provided information based on the results of quantitative analysis performed by the quantitation apparatus to the ion adsorbent which the adsorbent identification information retrieved by the retrieval unit is assigned.

Advantageous Effects of Invention

According to the present invention, performing an accurate quantitation of an ultra-trace amount of ionic impurities in the water being analyzed later and to facilitating the implementation of defect analysis can be made possible.

BRIEF DESCRIPTION OF DRAWINGS

FIG. 7 is a diagram showing an example of the association between the period information and the adsorbent identification information stored in the database shown in FIG. 6.

FIG. 8 is a diagram showing an example of the association between the installation information and the adsorbent identification information stored in the database shown in FIG. 6.

DESCRIPTION OF EMBODIMENTS

Figure 1:
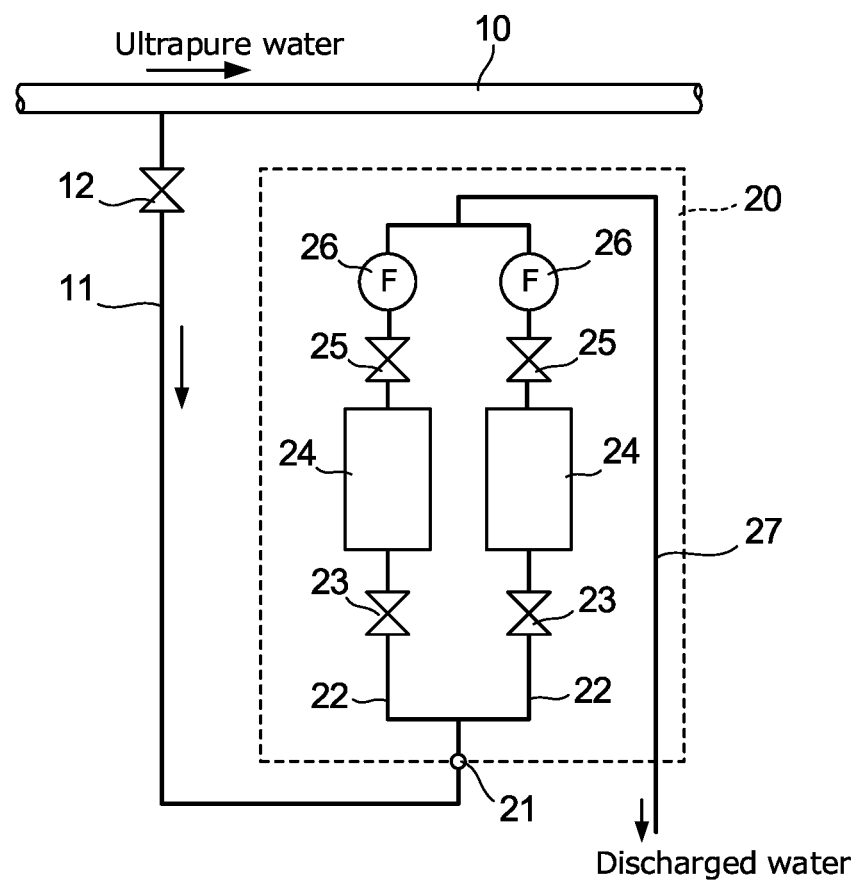
FIG. 1 is a diagram showing an ion adsorption device of an embodiment of the present invention.

Hereinafter, preferred embodiments of the present invention will be described with reference to the accompanying drawings. FIG. 1 shows an ion adsorption device of an embodiment of the present invention. Here, it is assumed that the water being analyzed is ultrapure water used in the manufacturing process of a product such as a semiconductor device and in contact with the product, but the water being analyzed to which the ion adsorption device or the water quality management method of the present invention is applied is not limited thereto.

Branch pipe 11 is branched from ultrapure water supply pipe 10 for supplying ultrapure water to the point of use, on-off valve 12 is provided in branch pipe 11. Ion adsorption device 20 is removably attached to the distal end of branch pipe 11 via fitting 21. As the ultrapure water in ultrapure water supply pipe 10 at the time of attachment and removal of ion adsorption device 20 is not contaminated, it is preferable that ion adsorption device 20 be attached to the pipe branched from ultrapure water supply pipe 10 (such as branch pipe 11).

Inside ion adsorption device 20, one or a plurality of internal pipes 22 are connected to fitting 21, the ultrapure water which is the water being analyzed is adapted to flow through the respective internal pipes 22 through fitting 21 from branch pipe 11. When providing a plurality of internal pipes 22, their internal pipes 22 are provided in parallel to each other. In the illustrated in FIG. 1, two internal pipes 22 are provided. For each internal pipe 22, ion adsorbent 24 is removably provided. In each internal pipe 22, taking into account the flow direction of the water being analyzed in internal pipe 22, on-off valve 23 is provided on the inlet side of ion adsorbent 24, flow rate adjusting valve 25 is provided on the outlet side of ion adsorbent 24, further the downstream side accumulated flow rate meter 26 for measuring the accumulated flow rate of the water being analyzed flowing through ion adsorbent 24 is provided. The outlet of each internal pipe 22 is connected to discharge pipe 27. Flow rate adjusting valve 25 performs conduction and shutoff of the water being analyzed, and a first valve capable of adjusting the flow rate of the water being analyzed, on-off valve 23 is a second valve that performs conduction and shutoff of the water being analyzed. The water being analyzed flowing through ion adsorbent 24 via internal pipe 22 and that is supplied via fitting 21 is finally discharged to the outside as discharged water through discharge pipe 27.

The function of ion adsorption device 20 of the present embodiment is to perform the quantifying of ionic impurities in the water being analyzed by the concentration method described above, and ionic adsorbent 24 captures ionic impurities such as metal ions in the water being analyzed as they flow from the branch pipe 11 into internal pipe 22. As ion adsorbent 24, a porous membrane having an ion exchange function, a column filled with a granular ion exchange resin, or the like can be used. However, it is preferable to use a monolithic organic porous ion exchanger as ion adsorbent 24 so that the differential pressure between the inlet and outlet does not increase even when water is passed at a high flow rate, and in order to prevent a short path that the water being analyzed flows by shorting the ion exchanger. As the monolithic organic porous ion exchanger, for example, a monolithic organic porous ion exchanger having a structure such as an open cell structure disclosed in Japanese Patent Laid-Open No. 2009-62412, a co-continuous structure disclosed in Japanese Patent Laid-Open No. 2009-67982, a particle aggregation type structure disclosed in Japanese Patent Laid-Open No. 2009-7550, and a particle composite type structure disclosed in Japanese Patent Laid-Open No. 2009-108294 can be used. Since the flow rate of the water being analyzed to ion adsorbent 24 can be increased by reducing the differential pressure in ion adsorbent 24 using the monolithic organic porous ion exchanger, and since the amount of adsorption of the ionic impurities to ion adsorbent 24 can be increased even if the concentration of the ionic impurities in the water to be analyzed is the same, the lower limit of quantification of the ionic impurities can be set to the lower concentration side.

Depending on the type of the metal ion contained in the being analyzed, some metal ions can be efficiently adsorbed on the cation exchanger and others which can be efficiently adsorbed on the anion exchanger. When the metal ion to be detected as an ionic impurity is not limited to a specific type, it is preferable to provide both ion adsorbent 24 containing a cation exchanger and ion adsorbent 24 containing an anion exchanger in ion adsorption device 20, for example, when a defect analysis of a product produced using ultrapure water is performed.

When the water to be analyzed is passed through ion adsorbent 24 for a predetermined period of time, the ionic impurities captured by ion adsorbent 24 are then eluted by an eluent, and the concentration of the ionic impurities transferred into the eluent is quantified. Ionic impurities in the water to be analyzed are concentrated in the eluent, but the concentration magnification is obtained by dividing the accumulated flow rate of water flow to ion adsorbent 24 by the volume of the eluent. Therefore, the accuracy of quantitation of ionic impurities in the water to be analyzed also depends on the accumulated flow rate flowing through ion adsorbent 24. Since the amount of water flow to ion adsorbent 24 also changes in accordance with the pressure fluctuation of the water to be analyzed, even if multiplied by the flow time to the flow rate as the flow rate was adjusted at the start of water flow does not always match the actual accumulated flow rate. Therefore, in ion adsorption device 20 of the present embodiment, accumulated flow rate meter 26 is provided in internal pipe 22 in order to determine the actual accumulated flow rate of the water to be analyzed flowing through ion adsorbent 24, so that the accurate accumulated flow rate value can be obtained. The provision of accumulated flow rate meter 26 on the downstream side of ion adsorbent 24 with respect to the flow direction of the water to be analyzed is to avoid the influence of foaming to be described later in order to avoid the influence of contamination from accumulated flow rate meter 26. Further, since the flow rate suitable for water flow is present when passing the water to be analyzed to each ion adsorbent 24, in order to use when adjusting the flow rate of the water to be analyzed to each ion adsorbent 24, it is preferable that accumulated flow rate meter 26 can measure the instantaneous flow rate. When adjusting the flow rate, the opening of flow rate adjusting valve 25 is adjusted while referring to the measured value of the instantaneous flow rate.

In order to improve reliability when continuous analysis is performed over a long period of time, it is also preferable that a plurality of ion adsorbents 24 be provided in ion adsorption device 20 so that the water to be analyzed flows in parallel to these ion adsorbents 24. In this case, since an accumulated flow rate for each ion adsorbent 24 is required for quantitation of ionic impurities, it is necessary to provide accumulated flow rate meter 26 for each ion adsorbent 24. Further, a plurality of ion adsorbents 24 may be provided in parallel with each other in ion adsorption device 20 so that the water to be analyzed can be simultaneously flowed through the plurality of ion adsorbents 24. By doing so, it is possible to simultaneously obtain a plurality of the same samples (adsorbents adsorbed with water to be analyzed) from each other, and therefore, if analysis is performed on the obtained plurality of samples, the reliability of the analysis result can be increased. Further, since a plurality of the same samples can be obtained from each other, it is also possible to cope with an unexpected situation such as a loss of a part of ion adsorbent 24 collected as a sample and a failure in quantitation due to an analysis apparatus failure.

Incidentally, in the ultrapure water used in the semiconductor device manufacturing must reduce the dissolved oxygen (DO) concentration to the limit, therefore, such as a tank provided in a path for circulating ultrapure water is filled with nitrogen gas so as to ensure that ultrapure water and oxygen do not come into contact with each other, in the ultrapure water circulating nitrogen is often dissolved to about partial pressure 0.1 MPa. The ultrapure water is usually pressurized and fed, so that when the pressure of ultrapure water, which is the water to be analyzed, decreases, bubbles of dissolved nitrogen are generated. When quantitation of ionic impurities in ultrapure water for manufacturing a semiconductor device is performed by using ion adsorption device 20 of the present embodiment and when bubbles are generated in ion adsorption device 20 and accumulate in ion adsorbent 24, partial blockage occurs inside ion adsorbent 24, and the surface area for adsorbing ionic impurities is reduced, and as a result, ionic impurities in the water to be analyzed cannot be completely captured. If the ionic impurities cannot be completely captured, the resulting quantitative results are also inaccurate. Therefore, a member that may result in a large pressure drop therein to ion adsorption device 20, i.e. flow rate adjusting valve 25 and accumulated flow rate meter 26, when viewed in the flow direction of the water being analyzed, is preferably provided on the downstream side of ion adsorbent 24. Further, in order that the bubbles are easily discharged outside the system even if bubbles are generated, particularly in internal pipe 22 of ion adsorption device 20, it is preferable that the water being analyzed flows in the upward flow.

Ion adsorption device 20 of the present embodiment is removed from branch pipe 11 after having passed water being analyzed over a predetermined period of time. As will be described later, quantitation of ionic impurities captured in ion adsorbent 24 may be performed immediately after removal, or may be performed after a certain amount of time has elapsed, or may be performed according to a later request. It is preferable to be able to completely close the inlet side and the outlet side of ion adsorbent 24 so that ion adsorbent 24 is not contaminated or so that the ionic impurities do not flow out of ion adsorbent 24 during the period from the time when the ion adsorbent is removed to the time when the quantitation is performed. Therefore, in ion adsorption device 20 of the present embodiment, on-off valve 23 described above is provided on the inlet side of ion adsorbent 24. Flow rate adjusting valve 25 also functions to fully close the outlet side of ion adsorbent 24.

Figure 2:
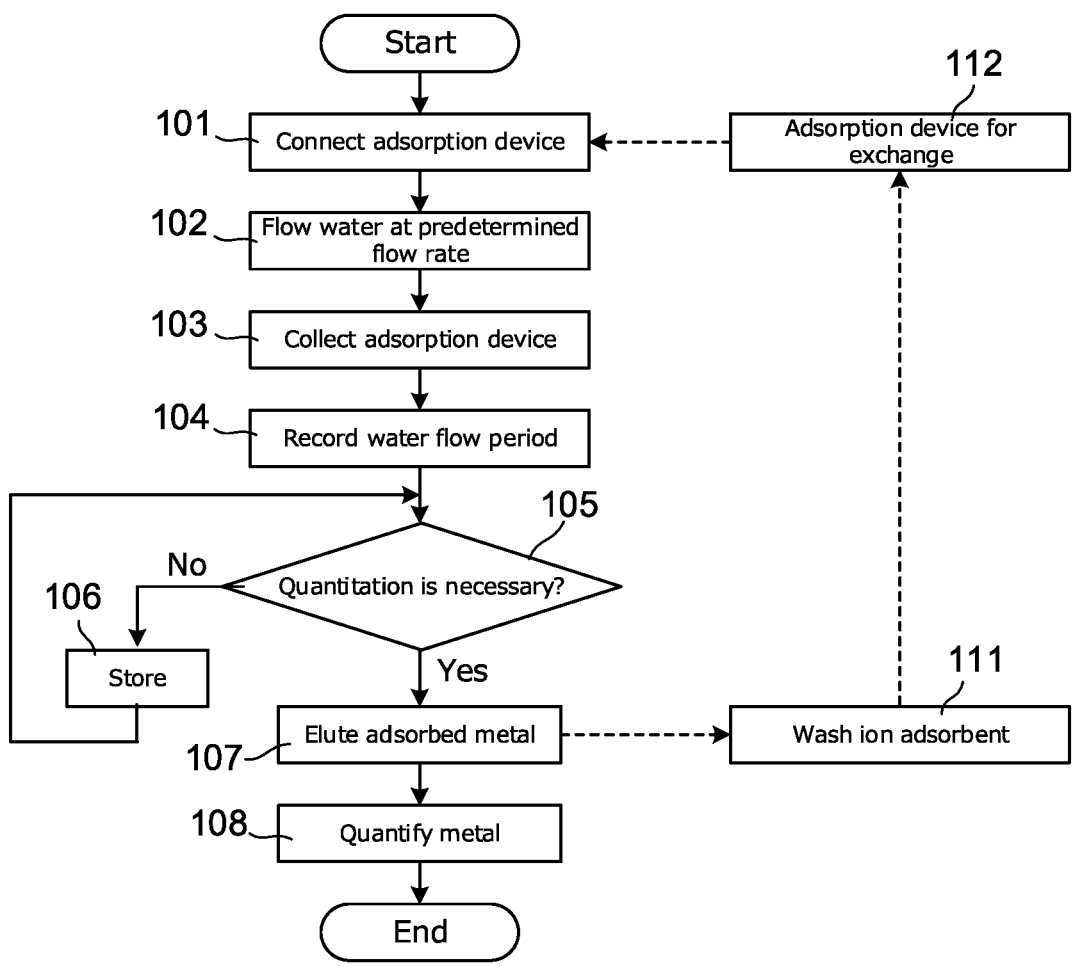
FIG. 2 is a flowchart for explaining the water quality management method.

Next, a water quality management method using this ion adsorption device 20 will be described with reference to FIG. 2. Here, it is assumed that the water quality control is performed by quantifying the metal ions contained as impurities in the ultrapure water flowing through ultrapure water supply pipe 10 as the water to be analyzed. First, blowing the like stagnant water remaining in branch pipe 11 by opening on-off valve 12 before ion adsorption device 20 is connected to branch pipe 11, once closing on-off valve 12, then, as shown in step 101, ion adsorption device 20 via fitting 21 is connected to branch pipe 11. Then, opening on-off valve 12, and opens on-off valve 23 and flow rate adjusting valve 25 in each internal pipe 22, as shown in step 102, to start flow of water to be analyzed to ion adsorbent 24. At this time, by adjusting the opening of flow rate adjusting valve 25 by measuring the instantaneous flow rate using the instantaneous flow measurement function of accumulated flow rate meter 26, the flow rate of the water being analyzed flowing through ion adsorbent 24 to a specified value is set. Then, when performing the flow of the water being analyzed to ion adsorbent 24 over a predetermined period, on-off valve 23 and flow rate adjusting valve 25 are closed, also on-off valve 12 is closed, ion adsorption device 20 is removed from branch pipe 11 as shown in step 103 to collect ion adsorption device 20. Ion adsorbent 24 in which an ionic impurity (here, a metal ion) is adsorbed by passing water being analyzed is also referred to as an ion adsorbent sample. FIG. 2 is a flowchart focusing on a particular ion adsorption device 20, after removing ion adsorption device 20 in step 103, at that time, by connecting ion adsorption device 20 for exchange to branch pipe 11 (step 101), it is possible to perform the management of water quality over a continuous period. Incidentally, when ion adsorption device 20 is not connected to branch pipe 11, on-off valve 12 is fully closed except when blowing the stagnant water in branch pipe 11. Further, when ion adsorption device 20 is not connected to branch pipe 11, so that the end portion and the inside of branch pipe 11 is not contaminated, it is preferable to close the tip of branch pipe 11.

Upon collecting ion adsorption device 20, in step 104, the period of time during which water is passed through ion adsorption device 20 (e.g., from the time of the month and days to the time of the month and days) is recorded. The recording may be, for example, a physical tag (e.g., a handwritten label, printed label or IC (integrated circuit) chip) to fill in or record the water flow period and attach to ion adsorption device 20, or, if a serial number or the like is given to ion adsorption device 20, the serial number and the water flow period may be managed on a database. In preparation for data loss in accumulated flow rate meter 26, it is preferable to also record the accumulated flow rate at that time. Thereafter, in step 105, it is determined whether it is necessary to perform quantitation of metal ions at present. Continuing to step 107 as quantitation is necessary if routine analysis is performed. If there is no need for quantitation at this time, but there is a possibility that the quantitation will be performed later for a failure analysis, then in step 106, ion adsorption device 20 is stored and the process returns to step 105. Although a case in which ion adsorption device 20 is stored in Step 106 has been described, ion adsorbent 24 may be taken out from ion adsorption device 20 to store ion adsorbent 24.

In step 107, ion adsorbent 24 is removed from ion adsorption device 20, for example, in a clean room, and elution of the adsorbed metal is performed by passing an eluent such as a strong acid or a strong base through the removed ion adsorbent 24, followed by quantitation of the metal using an eluent containing the eluted metal as a sample in step 108. As a quantitative analysis method, a general quantitative analysis method can be used, and examples thereof include, but are not limited to, plasma mass spectrometry (ICP-MS) method, plasma emission spectrometry (ICP) method, atomic absorption method, ion chromatography method, and the like.

By performing the quantitation of the metal in step 108, a series of processes for a certain 1 ion adsorption device 20 ends, but ion adsorption device 20 and ion adsorbent 24 itself can be reused. In order to be reused, ion adsorbent 24 after quantitation is washed as shown in step 111, and ion adsorbent 24, after washing is mounted on ion adsorption device 20 as shown in step 112 to be ion adsorption device 20 for exchange. This new replacement ion adsorption device 20 allows the process from step 101 to be performed again.

Figure 4:
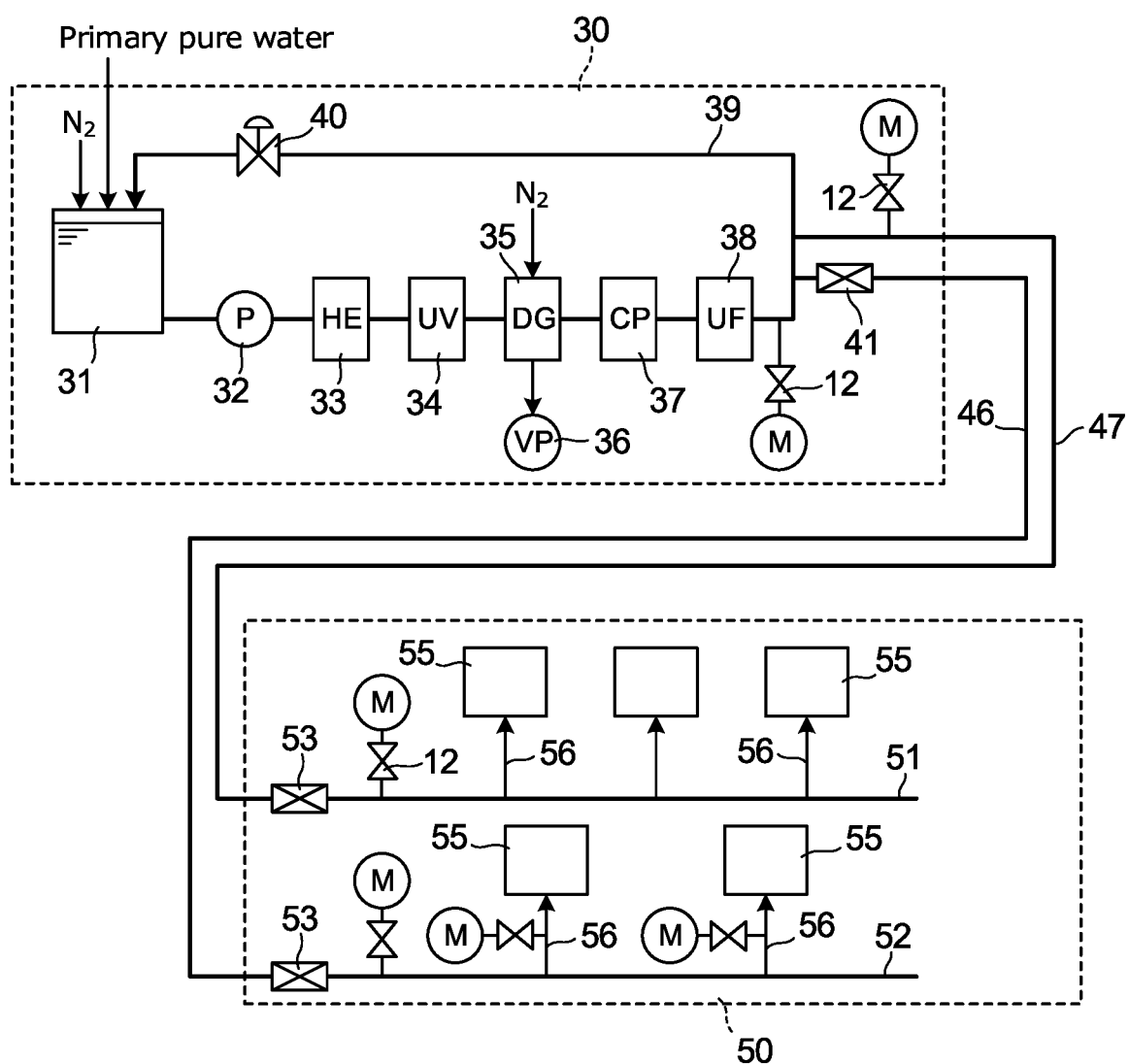
FIG. 4 is a diagram illustrating an example of a connection location of the ion adsorption device in a factory having a step of using ultrapure water.

A defect may occur in a product manufactured using ultrapure water, which is the water being analyzed, and it may be suspected that the cause of the defect is the quality of the ultrapure water. For example, in semiconductor device manufacturing, after cleaning the wafer using ultrapure water in the semiconductor cleaning step, the result of inspection of the wafer is performed after several steps and, if a defect of the wafer is detected, as a cause of the defect, ions contained in the ultrapure water at the time of wafer cleaning may be suspected. In other words, when a problem occurs in a product, it is determined that a quantitative analysis of an ion adsorbent sample of a water flow period corresponding to a time when a product uses water is necessary, and a quantitative analysis is performed. If an event suspected to be attributable to such ultrapure water occurs, for ion adsorption device 20 having a period corresponding to at least that event among ion adsorption device 20 stored in step 106 as the water flow period, it is determined that the quantitation is necessary in step 105 and the ion adsorbent sample of ion adsorption device 20 performs the elution of the adsorbed metal in step 107 and the quantitation of the metal in step 108. As a result, it is possible to judge whether or not the cause of the event such as the defect is metal ions in ultrapure water in the applicable period. Further, from the adsorbent information (described later) of the ion adsorbent sample subjected to quantitation, it is possible to specify where the cause of an event such as a defect generated in a product or the like is. For example, as shown in FIG. 4 (to be described later in detail), if ion adsorption device 20 is provided at the outlet of ultrafiltration membrane device 37 of ultrapure water production apparatus 30, the connection position between ultrapure water production apparatus 30 and supply pipe 47, the main pipes 51 and 52 of production building 50, branch pipes 56 connected from main pipes 51 and 52 to ultrapure water use device 55, or the like, it is possible to specify which device and which member cause an event such as a defect that occurred in a product or the like is based on the quantitation result and adsorbent information. Further, for example, if a plurality of ions adsorbing device 20 with respect to a long pipe as supply pipe 46 or supply pipe 47 of FIG. 4 are provided at predetermined intervals, similarly, it is also possible to identify which location of supply pipe 46 or supply pipe 47 is the cause of the event such as a defect occurring in the product or the like. Ion adsorption device 20 having a period corresponding to an event as a water flow period is ion adsorption device 20 of a water flow period including a period of time in contact with the water being analyzed when the water is in contact with the water being analyzed at any point in the past in the manufacturing process of the product in which an event has occurred. In addition, the water flow period here is information indicating when the date and time of water flow can be specified (the same applies to the following description). For example, the water flow period is information including at least one of a date and time at which water flow is started to ion adsorption device 20 and a date and time at which water flow is terminated.

In this embodiment, since the water flow period is recorded for each of ion adsorption devices 20, even when the occurrence of a defect is found later, it becomes possible to easily find and analyze ion adsorption device 20 in the water flow period corresponding to the defect from ion adsorption device 20 during storage. In order to perform a more precise failure analysis, it is preferable to not only perform the quantitation with respect to ion adsorption device 20 of the water flow period corresponding to the period in which the failure has occurred but also to perform the quantitation with respect to ion adsorption device 20 of the water flow period corresponding to the period before and after the period in which the failure has occurred.

According to the present embodiment, it is possible to manage the ultra-trace metal ions in the ultrapure water as a continuous quantitative value for each predetermined period of time, and when a yield decrease or the like of the manufactured article occurs, it becomes possible to quickly determine whether or not the cause of the yield decrease is derived from the ultrapure water by a comparison between the manufacturing process history of the product and the water permeation period to the ion adsorbent and the quantitative result of the metal ion.

Figure 3:
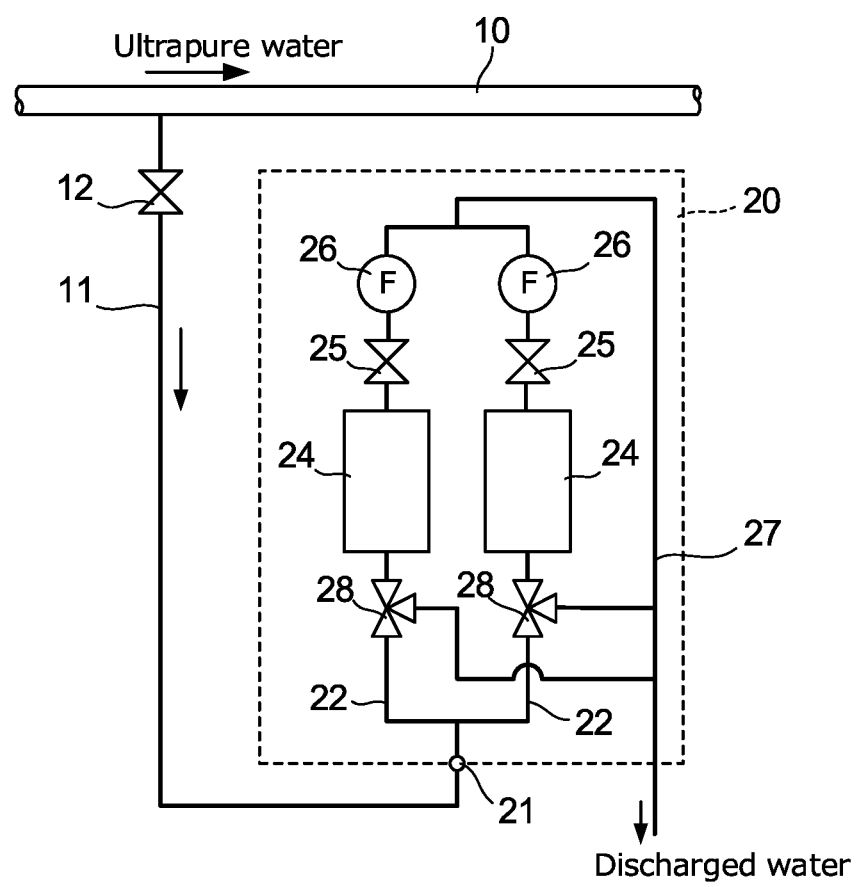
FIG. 3 is a diagram showing an ion adsorption device of another embodiment of the present invention.

Next, an ion adsorption device of another embodiment of the present invention will be described with reference to FIG. 3. In the example shown in FIGS. 1 and 2, the ion adsorption device is attached to branch pipe 11 after blowing such stagnant water remaining in branch pipe 11 by opening on-off valve 12. However, it may be difficult to directly blow branch pipe 11 depending on the site. As regards ion adsorption device shown in FIG. 3, by replacing on-off valve 23 in ion adsorption device 20 shown in FIG. 1 with three-way valve 28, so that it is possible to perform blowing of branch pipe 11 through the ion adsorption device itself. One outlet of three-way valve 28 is connected to the inlet of ion adsorbent 24, the other outlet is connected directly to discharge pipe 27, so that the destination of the water being analyzed supplied via fitting 21 can be switched between ion adsorbent 24 side and discharge pipe 27 side. When using ion adsorption device 20 shown in FIG. 3, and when connecting ion adsorption device 20 in a state of closing on-off valve 12 to branch pipe 11, three-way valve 28 to discharge pipe 27 side, so that the stagnant water is drained through discharge pipe 27 by opening on-off valve 12 thereafter. When the blowing of the stagnant water is completed, once three-way valve 28 is closed, then three-way valve 28 is switched to ion adsorbent 24 side, to start the flow of water being analyzed to ion adsorbent 24. Thereafter, it is sufficient to perform the procedure described with reference to FIG. 2.

Next, an example of applying the water quality control method described above to a semiconductor device manufacturing factory will be described. FIG. 4 is a flowsheet showing a portion of the production and consumption of ultrapure water in a semiconductor device manufacturing factory, shows an example of a connection location of ion adsorption device 20 in the semiconductor device manufacturing factory.

In the semiconductor device manufacturing factory shown, ultrapure water producing apparatus (secondary system pure water producing apparatus) 30 for producing ultrapure water primary pure water is supplied i.e. subsystem, and production building 50 is a place of actually using ultrapure water is provided separately. Ultrapure water producing apparatus 30 includes tank 31 for temporary storage receives the primary pure water, pump (P) 32 provided at the outlet of tank 31, heat exchanger (HE) 33 provided at the outlet of pump 32, ultraviolet oxidation device (UV) 34 for performing the steps for ultrapure water production, membrane deaerator (DG) 35, non-regenerative ion exchanger (CP) 37 and ultrafiltration membrane device (UF) 38, respectively. Ultraviolet oxidizer 34, membrane deaerator 35, non-regenerative ion exchanger 37 and ultrafiltration membrane device 38 are connected in series to the outlet of heat exchanger 33 in this order. Vacuum pump (VP) 36 is connected to membrane deaerator 35. Outlet water of ultrafiltration membrane device 38 is ultrapure water, a part of which is supplied to manufacturing building 50 via supply pipes 46 and 47, the remaining ultrapure water that has not been supplied to manufacturing building 50 is returned to tank 31 via circulation pipe 39. On circulation pipe 39, for example, in order to control the water pressure constant in the path in which the ultrapure water circulates, the valve 40 is provided. To minimize dissolved oxygen in ultrapure water to the limit, nitrogen ($N_2$) gas is supplied to tank 31 to purge oxygen. Since nitrogen sweep is performed together with removal of oxygen, nitrogen gas is also supplied to membrane degasser 35. The configuration and the arrangement of ultrapure water producing apparatus 30 is not limited to those shown.

At the position of ultrapure water producing apparatus 30 side of supply pipe 46 of supply pipe 46 and 47 to manufacturing building 50, ion adsorbent 41 is provided to capture ultra-trace amounts of ionic impurities in the ultrapure water. This ion adsorbent 41 may not be provided.

In manufacturing building 50, main pipes 51 and 52 to be connected respectively to supply pipes 46 and 47 are provided, a plurality of ultrapure water using device 55 with respect to main pipes 51 and 52 are connected via branch pipe 56, respectively. Ultrapure water using device 55 is, for example, a cleaning apparatus, an etching apparatus, an exposure apparatus, or the like. On an inlet side of main pipe 51 and 52, ion adsorbent 53 for capturing an ultra-trace amount of ionic impurities contained in ultrapure water supplied from supply pipe 46 and 47, respectively, is provided. This ion adsorbent 53 may not necessarily be provided.

An example of a location where ion adsorption device 20 can be provided is indicated by the reference numeral M in FIG. 4. That is, in ultrapure water producing apparatus 30, adsorption device 20 may be provided at the outlet of the ultrafiltration membrane device 37, and may be provided at a connection position with supply pipe 47. In manufacturing building 50, adsorption device 20 may be provided in each main pipe 51 and 52, and may be provided in branch pipe 56 connecting to the respective ultrapure water using device 55. The installation location and the number of installation of ion adsorption device 20 is not limited to those shown, and it is possible to install ion adsorption device 20 at any location. Each ion adsorption device 20 is connected to the pipe in which the ultrapure water flows through on-off valve 12 similarly to that shown in FIG. 1, when attaching or removing ion adsorption device 20, on-off valve 12 is fully closed, and on-off valve 12 is opened after attaching ion adsorption device 20. Preferably, the stagnant water is blown by opening on-off valve 21 before attaching ion adsorption device 20. Discharged water from ion adsorption device 20, if a system of the recovered water is provided in the semiconductor device factory, it is preferable to return discharged water from ion adsorption device 20 to the system of the recovered water.

Table 1 shows an example of the result of the water quality management performed using ion adsorption device 20 of the present embodiment. It is assumed that ion adsorption device 20 is installed in the pipe of the ultrapure water used for cleaning of the semiconductor device, ion adsorption device 20 was exchanged and recovered for every 5 days of water flow, and the quantitation of metal ions. The accumulated flow rate for each period, which is 5 days, was 1000 L each, and cleaning was performed for the intermediate processed products of the lot indicated by the "washed product lot number" in the table for each period. Then, the non-defective ratio of the product obtained from the intermediate processed product of each lot was determined. For ultrapure water used for cleaning process, TOC, resistivity, dissolved oxygen concentration, and number of fine particles are measured on-line. In the example shown here, the non-defective ratio of the product obtained from the intermediate processed product subjected to cleaning process during five days from May 16 to May 20 is worse than that of the other periods. Such reduction in the non-defective ratio may be found in the intermediate inspection of the manufacturing process, in some cases after the final product is obtained, or may be found in shipments of the product, for example, a few weeks after the cleaning process. The results of on-line measurements do not reveal any signs of defect occurrence, but the quantitative results of metals adsorbed on the ion adsorbent samples indicate that the concentration of calcium and iron in ultrapure water is high during the period when many defects occur, so it can be inferred that the cause of the defect is calcium and iron. When ion adsorption device 20 of the present embodiment is used, it is possible to perform the quantitation of the ion adsorbent sample in the past after the occurrence of a defect is found, thus it is possible to easily perform defect analysis.

TABLE 1

| Duration of water flow | May 1~ May 5 | May 6~ May 10 | May 11~ May 15 | May 16~ May 20 | May 21~ May 25 |
|---|---|---|---|---|---|
| Accumulated flow rate [L] | 1000 | 1000 | 1000 | 1000 | 1000 |
| Wash products Lot number | IY85G65~ IY92G70 | IY92G71~ IY97L50 | IY97L51~ IJ03P22 | IJ06P44~ UR18S55 | UR18S56~ UR73V86 |
| Ratio of non-defective products [go] | 98.8 | 98.8 | 99.0 | 87.6 | 96.0 |
| Adsorbed metal | For all of the metals | For all of the metals | For all of the metals | Ca: 0.08 ppt Fe: 0.14 ppt | For all of the metals |
| Quantitative results | to be quantified 0.01 ppt or less | to be quantified 0.01 ppt or less | to be quantified 0.01 ppt or less | All other metals 0.01 ppt or less | to be quantified 0.01 ppt or less |
| TOC | Less than 1 ppb | Less than 1 ppb | Less than 1 ppb | Less than 1 ppb | Less than 1 ppb |
| Resistivity [MΩ · cm] | 18.23 | 18.23 | 18.23 | 18.23 | 18.23 |
| Fine particles of 0.05 μm or more [pcs/mL] | Less than 0.1 | Less than 0.1 | Less than 0.1 | Less than 0.1 | Less than 0.1 |

Hereinafter, a method of utilizing the above-described ion adsorption device will be described by way of example.

First System Example

Figure 5:
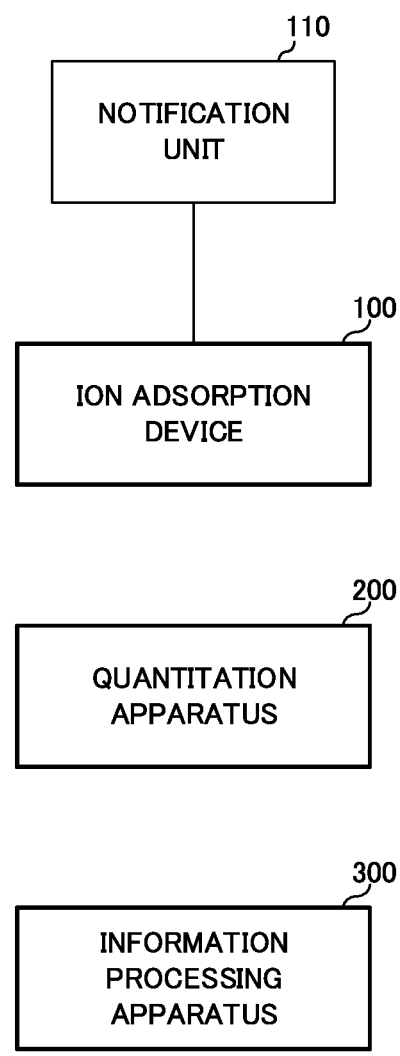
FIG. 5 is a diagram showing a first example of an information processing system utilizing the ion adsorption device shown in FIG. 1.

FIG. 5 is a diagram showing a first example of an information processing system utilizing ion adsorption device 20 shown in FIG. 1.

The information processing system shown in FIG. 5 includes ion adsorption device 100, quantitation apparatus 200, and information processing apparatus 300. Ion adsorption device 100 corresponds to ion adsorption device 20 shown in FIG. 1 or FIG. 3. Further, notification unit 110 is connected to ion adsorption device 100. Notification unit 110 performs a predetermined notification when a predetermined period has elapsed. Since the ion adsorbent provided in ion adsorption device 100 (ion adsorbent 24 shown in FIG. 1 or FIG. 3. hereinafter, the same.) is attached to the branch pipe (branch pipe 11 shown in FIG. 1 or FIG. 3. hereinafter, the same.), for example, it is a notification or the like indicating that. Or, notification unit 110 performs a predetermined notification when the accumulated value the accumulated flow rate meter provided in ion adsorption device 100 (accumulated flow rate meter 26 shown in FIG. 1 or FIG. 3. hereinafter, the same.) is measured becomes a predetermined value, after the ion adsorbent provided in the ion adsorption device 100 is attached to the branch pipe, for example, it is a notification or the like indicating that. At this time, notification unit 110 performs a notification prompting the removal of the ion adsorbent from the branch pipe. Notification unit 110 may be a unit that is provided inside ion adsorption device 100, it may be a unit that displays on a device such as another terminal device having an information display function. It is not necessarily provided with notification unit 110. For example, a plurality of ion adsorbents 24 provided in parallel with each other in ion adsorption device 20, when a predetermined period has elapsed after the ion adsorption device is attached to the branch pipe (specifically, after the water being analyzed flows to one ion adsorbent) or, when the accumulated value that the accumulated flow rate meter has measured, after the ion adsorption device is attached to the branch pipe, becomes a predetermined value, on-off valve 23 is automatically or manually switched, it is configured so that the water being analyzed flows to the other ion adsorbent, and the ion adsorbent may be removed from the branch pipe at a predetermined time.

Quantitation apparatus 200 performs quantitative analysis of the ion adsorbent to which ions are adsorbed. Specific methods of quantitative analysis are as described above. A method of identifying an ion adsorbent to be subjected to quantitative analysis will be described later.

Figure 6:
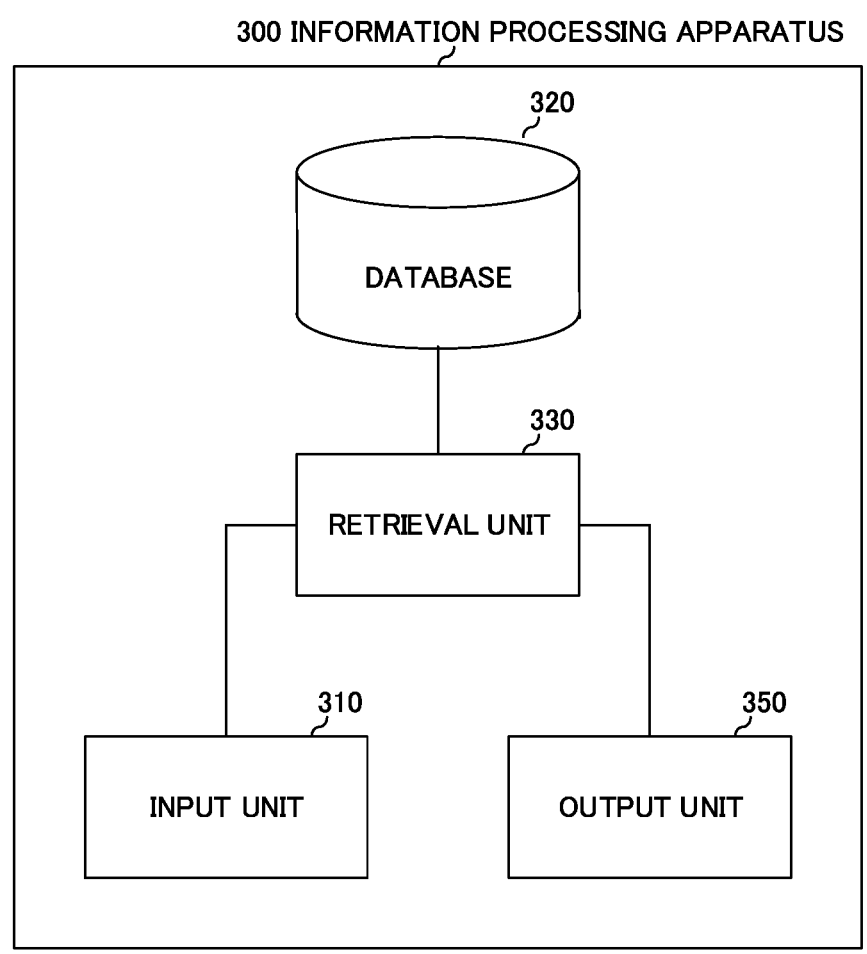
FIG. 6 is a diagram showing an example of the internal configuration of the information processing apparatus shown in FIG. 5.

FIG. 6 is a diagram showing an example of an internal configuration of information processing apparatus 300 shown in FIG. 5. Information processing apparatus 300 shown in FIG. 5 includes input unit 310, database 320, retrieval unit 330, and output unit 350 as shown in FIG. 6. Incidentally, in FIG. 6, among the components provided by information processing apparatus 300 shown in FIG. 5, only the main elements relate to the present embodiment.

Input unit 310 inputs the input information to information processing apparatus 300 based on the operation received from the outside. Specifically, input unit 310 receives a predetermined operation from the outside, and inputs information based on the received operation. The information that input unit 310 inputs, for example, is the information instructing the retrieval of the ion adsorbent sample, when defects of the wafer are detected in the semiconductor device manufacturing process and it is determined that it is necessary to perform a quantitative analysis of the ion adsorbent sample of the water flow period corresponding to the time of using the wafer cleaning water. Input unit 310 may be, for example, a keyboard, a mouse, a touch panel, or the like. Input unit 310 may display a GUI (Graphical User Interface) prompting input of predetermined information, and input information based on an operation performed according to the display. Further, information recorded by ion adsorption device 100 and information notified by notification unit 110 is transmitted to information processing apparatus 300, the input unit 310 may be an input unit that is input by receiving the transmitted information.

Database 320 associates a period information (including information such as the date and time when the water flow was started and the date and time when the water flow was completed to the ion adsorbent) indicating the period (the period in which water is passed through the ion adsorbent) in which the ion adsorbent was attached to the branch pipe with the adsorbent identification information assigned to the ion adsorbent inherent and stores it as the adsorbent information. Further, database 320 stores the installation information of ion adsorption device 100 to which the ion adsorbent is attached and the adsorbent information in association with each other. The method of registering the information to database 320 is not particularly limited. For example, when registering the period information, information including the date and time at the time of opening and closing on-off valve 23 is transmitted to database 320, may be stored as period information (registered). Further, when registering the period information, information including the date and time at the time when the water being analyzed starts to flow to the accumulated flow rate meter 26 and the time when the flow ends may be transmitted to the database 320, and stored as period information (registered). In addition, when the adsorbent identification information is registered, an identification tab such as a bar code or a two-dimensional code may be attached to ion adsorbent 24, and the attached identification tab may be read by the code reader (reading device), and the read information may be transmitted to database 320 and stored (registered) as the adsorbent information.

FIG. 7 is a diagram showing an example of the association between the installation information and the adsorbent information stored in database 320 shown in FIG. 6. Database 320 shown in FIG. 6, as shown in FIG. 7, "customer No.", "system No". and "device No.", and "adsorbent information" the position where the ion adsorbent is attached ion adsorption device 100 is installed can be identified is stored in association. The "customer No.", "system No." and "device No." are set up information for these together. "Customer No." is customer identification information assigned customer-specific to which ion adsorption device 100 to which the ion adsorbent is attached is installed. "System No." is the system identification information assigned to the system specific constructed in the customer's facility. "Device No." indicates device to which ion adsorption device 100 is installed in the system, a device identification information assigned to the installed device specific. Thus, by using the "customer No.", "system No." and "device No.", it is possible to identify the installation position of ion adsorption device 100 to which ion adsorbent is attached. Details of the adsorbent information will be described later.

For example, as shown in FIG. 7, the customer No. "A001", the system No. "1", the device No. "1", and the adsorbent information "A001-1-1" are stored in association with each other. This indicates that the ion adsorbent indicated by the adsorbent information "A001-1-1" is attached to the device to which the device identification information "1" is assigned installed in the system to which the system identification information "1" is assigned constructed in the facility of the customer to which the customer identification information "A001" is assigned. Further, the customer No. "A001", the system No. "1", the device No. "2", and the adsorbent information "A001-1-2" are stored in association with each other. This indicates that the ion adsorbent indicated by the adsorbent information "A001-1-2" is attached to the device to which the device identification information "2" is assigned installed in the system to which the system identification information "1" is assigned constructed in the facility of the customer to which the customer identification information "A001" is assigned. Further, the customer No. "A001", the system No. "2", the device No. "1", and the adsorbent information "A001-2-1" are stored in association with each other. This indicates that the ion adsorbent indicated by the adsorbent information "A001-2-1" is attached to the device to which the device identification information "1" is assigned installed in the system to which the system identification information "2" is assigned constructed in the facility of the customer to which the customer identification information "A001" is assigned. Further, the customer No. "A001", the system No. "2", the device No. "2", and the adsorbent information "A001-2-2" are stored in association with each other. This indicates that the ion adsorbent indicated by the adsorbent information "A001-2-2" is attached to the device to which the device identification information "2" is assigned installed in the system to which the system identification information "2" is assigned constructed in the facility of the customer to which the customer identification information "A001" is assigned.

FIG. 8 is a diagram showing an example of the association between the period information and the adsorbent identification information stored in database 320 shown in FIG. 6. This association is the adsorbent information described above. The adsorbent information shown in FIG. 8 is one of the adsorbent information items shown in FIG. 7 (adsorbent information "A001-1-1"), and when nine adsorbent information items are stored in database 320 as shown in FIG. 7, nine adsorbent information items that are associated, as shown in FIG. 8 are stored in database 320. Thus, for example, the adsorbent information shown in FIG. 8 corresponds to one "A001-1-1" of the adsorbent information items shown in FIG. 7.

In database 320 shown in FIG. 6, as shown in FIG. 8, a "period" which is period information indicating a period in which the ion adsorbent has been attached to ion adsorption device 100, a "flow rate [L]" which is an accumulated amount of water flow in the period, and an "adsorbent No." which is adsorbent identification information assigned to the ion adsorbent proper are associated with each other, and are stored as one item of adsorbent information. Incidentally, the flow rate is the accumulated value measured by the accumulated flow rate meter in that period.

For example, as shown in FIG. 8, the period "2019 May 1~2019 May 5", the flow rate "1000 [L]" and adsorbent No. "A00010001" are stored in association with each other. This indicates that the ion adsorbent to which the adsorbent identification information "A00010001" has been assigned has been attached to ion adsorption device 100 for five days from May 1, 2019 to May 5, 2019, during which time the amount of water being analyzed flows into the ion adsorbent is 1000 [L]. Further, the period "2019 May 6~ 2019 May 10", the flow rate "980 [L]" and adsorbent No. "A00020001" are stored in association with each other. This indicates that the ion adsorbent to which the adsorbent identification information "A00020001" has been assigned has been attached to ion adsorption device 100 for five days from May 6, 2019 to May 10, 2019, during which time the amount of water being analyzed flows into the ion adsorbent is 980 [L]. Further, the period "2019 May 11~2019 May 15", the flow rate "1000 [L]" and adsorbent No. "A00030001" are stored in association with each other. This indicates that the ion adsorbent to which the adsorbent identification information "A00030001" has been assigned has been attached to ion adsorption device 100 for five days from May 11, 2019 to May 15, 2019, during which time the amount of water being analyzed flows into the ion adsorbent is 1000 [L]. Further, the period "2019 May 16~2019 May 20", the flow rate "990 [L]" and adsorbent No. "A00040001" are stored in association with each other. This indicates that the ion adsorbent to which the adsorbent identification information "A00040001" has been assigned has been attached to ion adsorption device 100 for five days from May 16, 2019 to May 20, 2019, during which time the amount of water being analyzed flows into the ion adsorbent is 990 [L]. These associations are registered and stored after the respective ion adsorbent is removed from ion adsorption device 100. The registration method may be one in which this information is transmitted from ion adsorption device 100 to information processing apparatus 300 and is registered, it may be one that registers via another medium. Incidentally, in the example shown in FIG. 6, "period" is period information that only shows the information indicating the date, but also includes information indicating the date and time including the time. In other words, the period information includes information indicating the date and time at which the ion adsorbent is attached to ion adsorption device 100 and information indicating the date and time at which the ion adsorbent is removed from ion adsorption device 100.

Retrieval unit 330 retrieves the adsorbent identification information from database 320 based on the date and time information (information regarding the time when the product uses water when a problem occurs in the product) included in the input information input by input unit 310. Specifically, retrieval unit 330 retrieves a period including the date and time indicated by the date and time information included in the input information input by input unit 310 from database 320, and retrieves the adsorbent identification information associated with the retrieved period from database 320. At this time, retrieval unit 330 retrieves the adsorbent information from database 320 based on the installation information of the ion adsorption device, which is included in the input information input by input unit 310, and retrieves the adsorbent identification information from database 320 based on the retrieved adsorbent information and the date and time information. For example, if the customer No. of the installation information included in the input information is "A001", the system No. is "1", and the device No. is "1", and the date and time information is "May 3, 2019", retrieval unit 330 retrieves the adsorbent information in which the customer No. is "A001", the system No. is "1" and the device No. is "1" from database 320, and from the correspondence of the retrieved adsorbent information "A001-1-1" retrieves the adsorbent No. "A00010001" associated with the period "2019 May 1 to 2019 May 5" including date and time information "May 3, 2019".

The system configuration in the customer's facility may be registered in database 320 in advance, and retrieval unit 330 may perform retrieval based on the configuration of the system. That is, for example, if it is considered that the device of the customer No. "A001", the system No. "1" and the device No. "1", and the device of the customer No. "A001", the system No. "1" and the device No. "2" may affect each other from the configuration of the system, the customer No. is "A001", the system No. is "1", and the device No. "1" of the installation information included in the input information, the retrieval unit 330 may also retrieve the adsorbent information about the device of the customer No. "A001", the system No. "1" and the device No. "2". Here, in order to determine whether or not there is an influence on each other, a determination model may be generated using machine learning based on the configuration of the system and the past determination result, and the determination may be performed using the determination model. For example, the device of the customer No. "A001", the system No. "1" and the device No. "1", and the device of the customer No. "A001", the system No. "1" and the device No. "2" are installed side by side in series, or from the previous analytical results, when a relationship is recognized between the analytical results of each other, etc., it may be a device that determines whether there is an effect on each other. Thus, by performing an analysis on devices that affect each other, it is possible to identify which of the plurality of devices provided in the system is generating pollutants, that is, the device generating the pollutants, when the cause of the product defects was the pollutants contained in the ultrapure water.

Output unit 350 outputs the adsorbent identification information retrieved by retrieval unit 330. The output method of the adsorbent identification information performed by output unit 350 may be, for example, transmission to another device, a screen display, audio output, or printing.

The information processing method in the information processing system shown in FIG. 5 will be described below.

Figure 9:
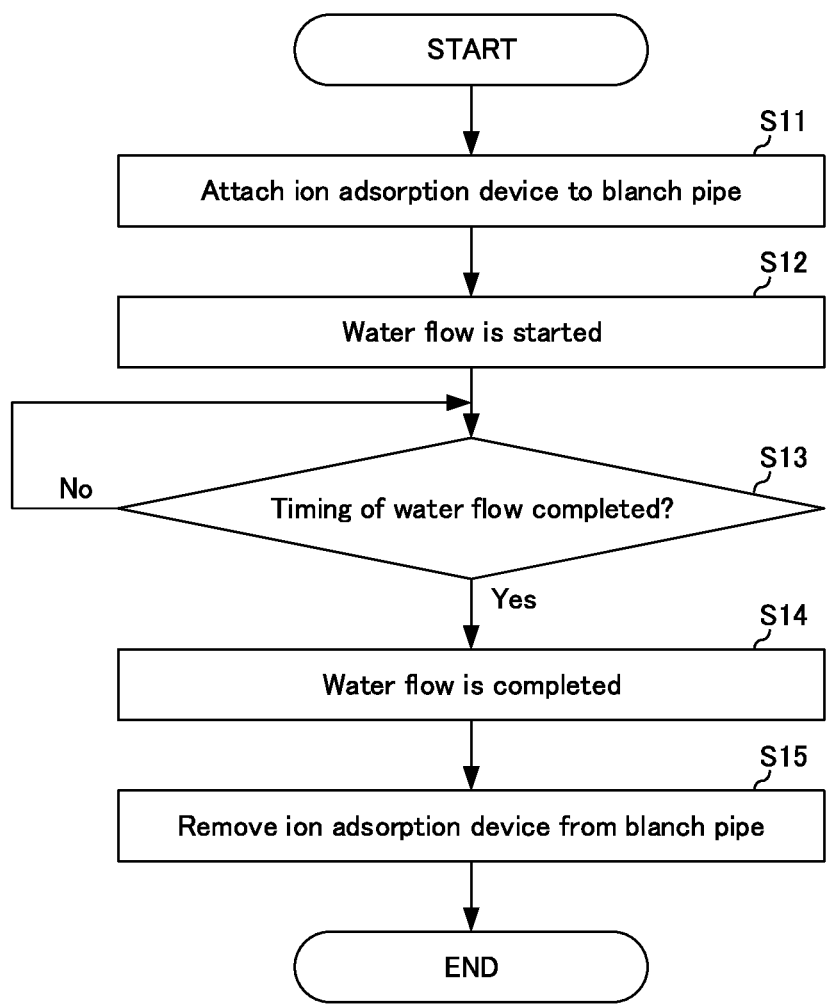
FIG. 9 is a flowchart for explaining an example of processing in the ion adsorption device among the information processing method in the information processing system shown in FIG. 5.

FIG. 9 is a flowchart for explaining an example of processing in the ion adsorption device 100 among the information processing methods in the information processing system shown in FIG. 5.

First, ion adsorption device 100 which is attached to the ion adsorbent is attached to branch pipe 11 (step S11). Subsequently, the water flow to branch pipe 11 is started (step S12). At this time, after ion adsorption device 100 is attached to branch pipe 11, on-off valve 23, flow rate adjusting valve 25, three-way valve 28 and on-off valve 12 shown in FIG. 1 or FIG. 3 are opened and the water flow to the ion adsorbent is started.

Thereafter, it is determined whether or not the timing of the end of the water flow is determined (step S13). Here, when a predetermined period has elapsed from the start of the water flow, or when the accumulated value of the water flow amount reaches a predetermined value, a determination is made of the timing when the water flow ends. The lapse of a predetermined period may be measured using a timer. The measurement of the accumulated value of the water flow may be performed using an accumulated flow rate meter. Notification unit 110 may notify the manager, the operator and the maintenance person (hereinafter, referred to as the manager or the like) of the system in the display or the like of detecting the timing at this timing. Thereafter, the water flow to branch pipe 11 is completed (step 14). At this time, on-off valve 23 shown in FIG. 1 or FIG. 3, flow rate adjusting valve 25, three-way valve 28 and the on-off valve 12 are closed. In addition, the person receiving the notification closes the valve. Then, ion adsorption device 100 is removed from branch pipe 11 (step S15). At this time, a new ion adsorption device 100 is attached to branch pipe 11. Further, the timer and the accumulated flow rate meter, each time ion adsorption device 100 that is attached to branch pipe 11 (replaced), are reset. Incidentally, the time from the timing of the removal of ion adsorption device 100 to the timing of attachment of the new ion adsorption device 100 should be as short as possible so as to ensure the continuity of the water permeation period with respect to the ion adsorbent.

Information such as the water passing period of the ion adsorbent provided in the removed ion adsorption device is stored in database 320 of information processing apparatus 300. The stored information is information as shown in FIG. 8, each of a plurality of information items for each one ion adsorbent is stored in association with each other. This storage is performed through input unit 310 of information processing apparatus 300. Further, the ion adsorbent provided in the removed ion adsorption device is stored in a predetermined storage place in which the adsorbent identification information is assigned.

Thereafter, when the quantitative analysis is required, a retrieval request is made to information processing apparatus 300. Here, it is necessary to perform quantitative analysis when a defect occurs in a product or the like produced using ultrapure water which is the water to be analyzed, and when it is confirmed whether or not the cause of the defect is in the water quality of ultrapure water. To do so, it is necessary to retrieve the ion adsorbent sample of interest (i.e., the ion adsorbent sample that has been passed through the water flow period corresponding to the time when the product has used water when a problem occurs in the product).

Figure 10:
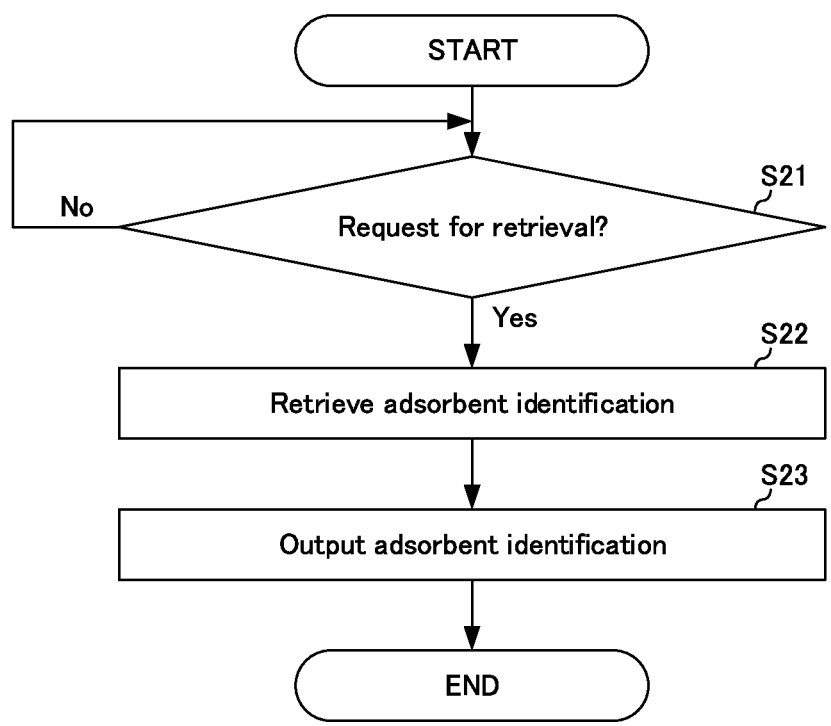
FIG. 10 is a flowchart for explaining an example of the retrieval processing in the information processing apparatus among the information processing methods in the information processing system shown in FIG. 5.

FIG. 10 is a flowchart for explaining an example of retrieval processing in the information processing apparatus among the information processing methods in the information processing system shown in FIG. 5.

Input unit 310 determines whether or not there is a request for retrieval of the ion adsorbent (step S21). This request may be based on the predetermined operation that the manager of the system or the like has performed for requesting the retrieval of the ion adsorbent to input unit 310 and input unit 310 has received. This predetermined operation includes the installation information and the date and time information of the target device (device of failure occurrence). Input unit 310 outputs the installation information and the date and time information among the input information items to retrieval unit 330. Retrieval unit 330 retrieves the adsorbent identification information from database 320 based on the installation information and the date and time information output from input unit 310 (Step S22). Specifically, for example, retrieval unit 330 retrieves the adsorbent information from database 320 based on the installation information output from input unit 310, and among the retrieved adsorbent information, retrieves the adsorbent identification information associated with a period including the date and time information output from input unit 310 from database 320. Then, output unit 350 outputs the adsorbent identification information retrieved by retrieval unit 330 (step S23).

Thereafter, an ion adsorbent to which the adsorbent identification information output from output unit 350 is assigned is secured from the storage place by an operator or the like, and quantitation is performed using quantitation apparatus 200. Then, the impurity ion concentration in the water being analyzed is calculated using the result of the quantitative analysis and the accumulated value measured by the accumulated flow rate meter. The result of the quantitation and the concentration of impurity ions in the water being analyzed are provided from the operator or the like to the desired destination.

Thus, in the system for performing water quality management, the ion adsorption device provided with the ion adsorbent is exchanged at a predetermined timing, the ion adsorbent that is provided in the removed ion adsorption device is stored, among the stored ion adsorbent, the ion adsorbent that is attached to the ion adsorption device attached at the specified installation location and period is retrieved, and quantitative analysis of the retrieved ion adsorbent is performed to provide the results. Therefore, it is possible to recognize the process status of the water to be analyzed at the specified location and date and time.

Second System Example

Figure 11:
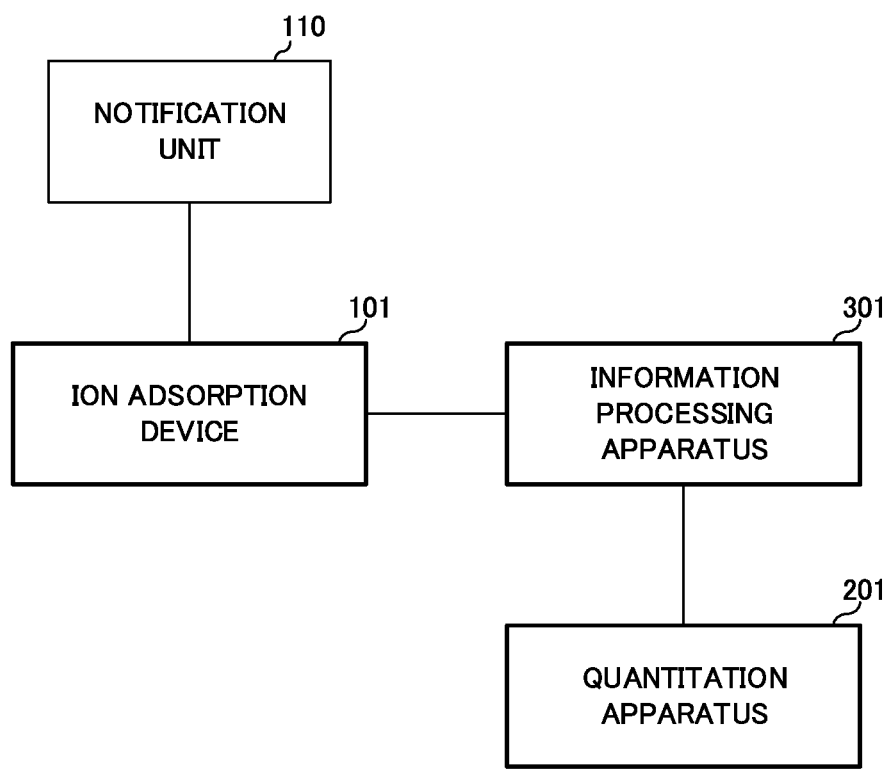
FIG. 11 is a diagram showing a second example of an information processing system utilizing the ion adsorption device shown in FIG. 1.

FIG. 11 is a diagram showing a second example of an information processing system utilizing ion adsorption device 20 shown in FIG. 1.

The information processing system shown in FIG. 11 has ion adsorption device 101, quantitation apparatus 201, and information processing apparatus 301. Ion adsorption device 101 corresponds to ion adsorption device 20 shown in FIG. 1 or FIG. 3. Further, ion adsorption device 101 transmits the date and time information of attachment to the branch pipe of the ion adsorbent and the date and time information of removal from the branch pipe of the ion adsorbent and the identification information of the ion adsorbent to information processing apparatus 301. Further, notification unit 110 is connected to ion adsorption device 101. Notification unit 110, when a predetermined period has elapsed since the ion adsorbent provided in the ion adsorption device 101 was attached to the branch pipe, performs a predetermined notification, for example, a notification or the like indicating that. Or, notification unit 110, when the accumulated value of the accumulated flow rate meter provided in ion adsorption device 101 measured becomes a predetermined value after the ion adsorbent provided in ion adsorption device 101 has been attached to the branch pipe performs a predetermined notification, for example, a notification or the like indicating that. At this time, notification unit 110 performs a notification prompting to remove the ion adsorbent from the branch pipe. Notification unit 110 may be one provided inside ion adsorption device 101, it may be one that makes a display on a device such as another terminal device having an information display function.

Quantitation apparatus 201 performs quantitative analysis of ions adsorbed on the ion adsorbent. Specific methods of quantitative analysis are as described above. A method of identifying an ion adsorbent to be subjected to quantitative analysis will be described later. Quantitation apparatus 201 provides a result of performing quantitative analysis to information processing apparatus 301. The providing method may be one in which quantitation apparatus 201 transmits information indicating the analysis result to information processing apparatus 301, or it may be one in which quantitation apparatus 201 provides via another medium.

Figure 12:
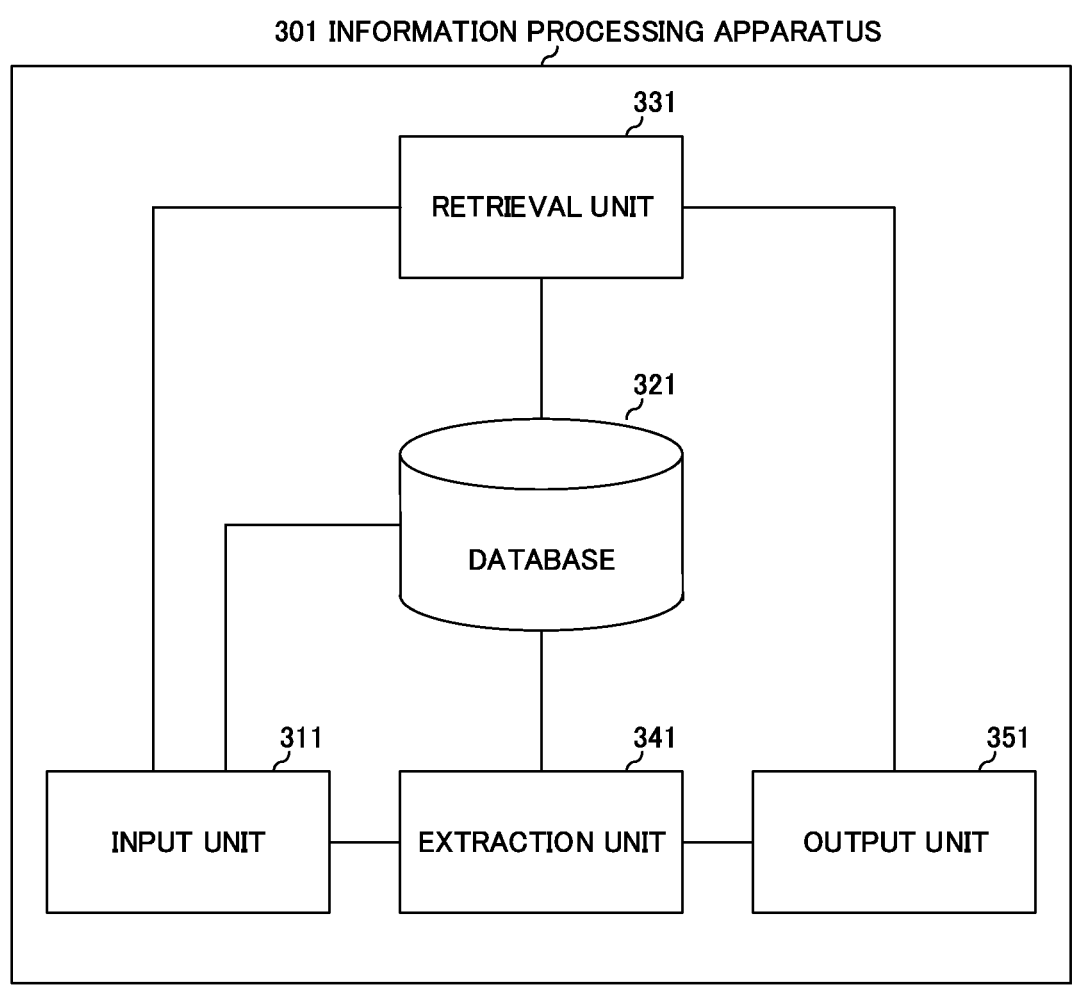
FIG. 12 is a diagram showing an example of the internal configuration of the information processing apparatus shown in FIG. 11.

FIG. 12 is a diagram showing an example of an internal configuration of information processing apparatus 301 shown in FIG. 11. Information processing apparatus 301 shown in FIG. 11 includes input unit 311, database 321, retrieval unit 331, extraction unit 341, and output unit 351, as shown in FIG. 12. Incidentally, in FIG. 12, among the components provided by information processing apparatus 301 shown in FIG. 11, only the main elements relating to the present embodiment are shown.

Input unit 311 inputs the input information to information processing apparatus 301 based on the operation received from the outside. Specifically, input unit 311 receives a predetermined operation from the outside, and inputs information based on the received operation. The information that input unit 311 inputs, for example, is the information instructing the retrieval of the ion adsorbent sample, when defects of the wafer are detected in the semiconductor device manufacturing process and a determination is made that it is necessary to perform a quantitative analysis of the ion adsorbent sample of the water flow period that corresponds to the time of using the wafer cleaning water. Input unit 311 may be, for example, a keyboard, a mouse, a touch panel, or the like. Input unit 311 may display a GUI prompting input of predetermined information, and input information based on an operation performed according to the display. Further, information recorded by ion adsorption device 101 and information that is notified by notification unit 110 are transmitted to information processing apparatus 301, the input unit 311 may be one that is input by receiving the transmitted information.

Database 321 stores the period information indicating the water flow period (including the date and time at which water flow was started, the date and time at which water flow was completed to the ion adsorbent, and the like) and the adsorbent identification information assigned to the ion adsorbent inherent in the ion adsorbent as the adsorbent information in association with each other. Further, database 321 stores the installation information of ion adsorption device 101 to which the ion adsorbent is attached and the adsorbent information in association with each other. The storage aspect of this information is the same as that shown in FIGS. 7 and 8. In addition, for example, database 321 may store an analysis result transmitted from quantitation apparatus 201 when a quantitative analysis is performed by determining that a quantitative analysis of an ion adsorbent sample of a water flow period that corresponds to a time when a product uses water when a problem occurs in a product. At that time, the analysis result transmitted from quantitation apparatus 201 is stored in database 321 via input unit 311.

Retrieval unit 331 retrieves the adsorbent identification information from database 321 based on the date and time information included in the input information input by input unit 311. Specifically, retrieval unit 331 retrieves a period including the date and time indicated by the date and time information included in the input information input by input unit 311 from database 321, and retrieves the adsorbent identification information associated with the retrieved period from database 321. At this time, retrieval unit 331 retrieves the adsorbent information from database 321 based on the installation information of the ion adsorption device, which is included in the input information input by input unit 311, and retrieves the adsorbent identification information from database 321 based on the retrieved adsorbent information and the date and time information. For example, if the customer No. of the installation information included in the input information is "A001", the system No. is "1", and the device No. is "1", and the date and time information is "May 3, 2019", retrieval unit 331 retrieves the adsorbent information in which the customer No. is "A001", the system No. is "1" and the device No. is "1" from database 321, and from the correspondence of the retrieved adsorbent information "A001-1-1", retrieves the adsorbent No. "A00010001" associated with the period "2019 May 1 to 2019 May 5" including date and time information "May 3, 2019".

The system configuration in the customer's facility may be registered in database 321 in advance, and retrieval unit 331 may perform retrieval based on the configuration of the system. That is, for example, if it is considered that the device of the customer No. "A001", the system No. "1" and the device No. "1", and the device of the custom No. "A001", the system No. "1" and the device No. "2" may affect each other from the configuration of the system, the customer No. is "A001", the system No. is "1", and the device No. "1" of the installation information included in the input information, retrieval unit 331 may also retrieve the adsorbent information about the device of the customer No. "A001", the system No. "1" and the device No. "2". Here, in order to determine whether or not there is an influence on each other, a determination model may be generated using machine learning based on the configuration of the system and the past determination result, and the determination may be performed using the determination model. For example, the device of the customer No. "A001", the system No. "1" and the device No. "1", and the device of the customer No. "A001", the system No. "1" and the device No. "2" are installed side by side in series, or from the previous analytical results, when a relationship is recognized between the analytical results of each other, etc., the relationship may be one that determines whether there is an effect on each other. Thus, by performing an analysis on devices that affect each other, it is possible to identify which of the plurality of devices provided in the system is generating pollutants, that is, the device that is generating the pollutants, when the cause of the product defects was the pollutants contained in the ultrapure water.

Extraction unit 341 extracts the provided information which is information corresponding to the input information from the result of the quantitative analysis provided (transmitted) from quantitation apparatus 201 with respect to the ion adsorbent to which the adsorbent identification information retrieved by retrieval unit 331 is assigned. Here, the input information, for example, may include a specific analysis content. In this case, extraction unit 341 extracts the result corresponding to the analysis content contained in the input information from the result of the quantitative analysis performed by quantitation apparatus 201. When the quantitative analysis provided (transmitted) from quantitation apparatus 201 is stored in database 321, extraction unit 341 extracts the provided information, which is information corresponding to the input information, from the result of the quantitative analysis stored in database 321.

Output unit 351 outputs the adsorbent identification information retrieved by retrieval unit 331. Output unit 351 outputs the result of the quantitative analysis performed by quantitation apparatus 201 to the ion adsorbent to which the adsorbent identification information retrieved by retrieval unit 331 is assigned as the provided information. Further, output unit 351, when extraction unit 341 extracts the provision information which is the information corresponding to the input information from the result of the quantitative analysis performed by quantitation apparatus 201, outputs the provision information extracted by extraction unit 341. The output method of the provided information performed by output unit 351 may be, for example, transmission to another device, a screen display, audio output, printing, and may be a predetermined lamp lighting or blinking.

Figure 13:
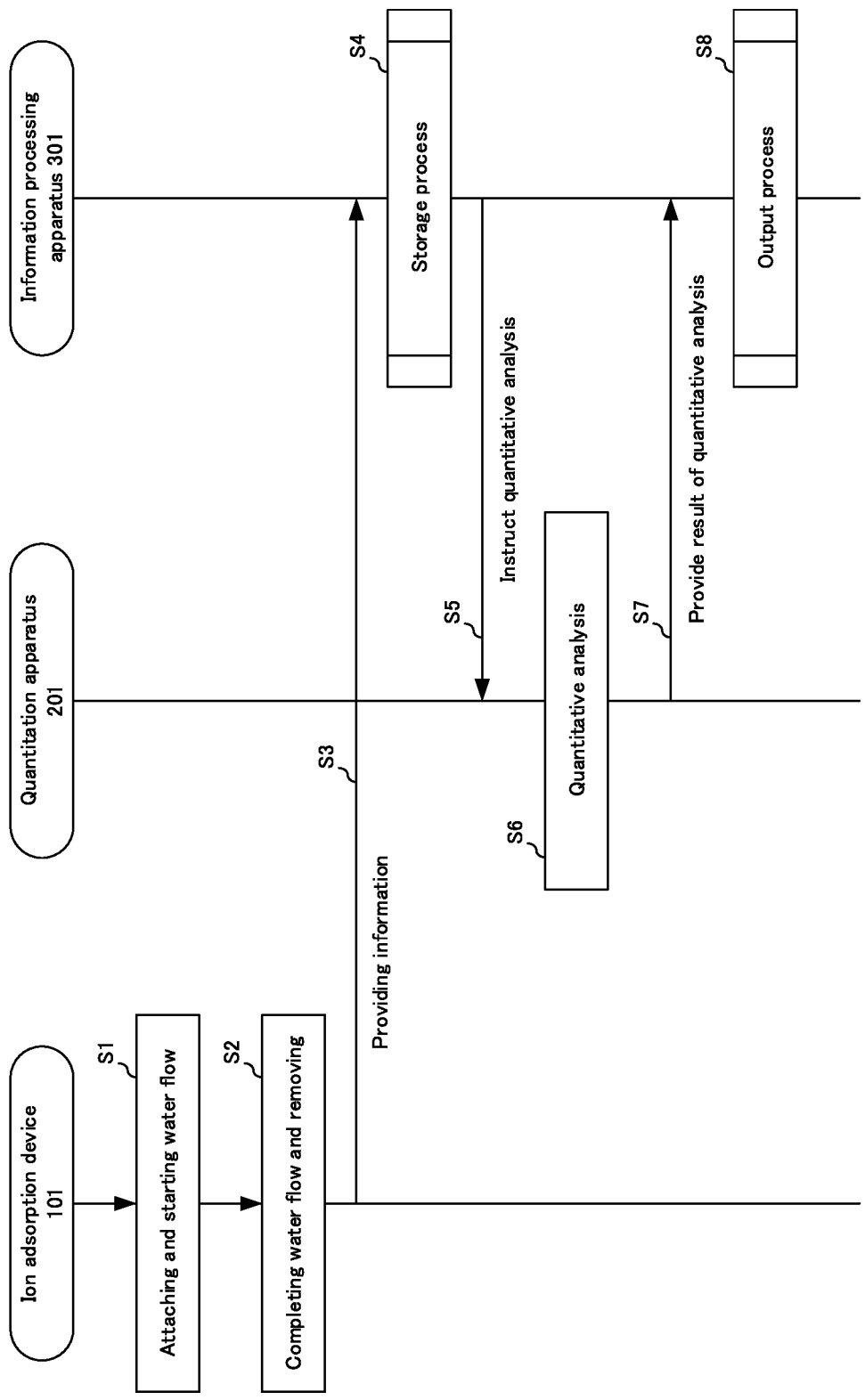
FIG. 13 is a sequence diagram for explaining an example of an information processing method in the information processing system shown in FIG. 11.

FIG. 13 is a sequence diagram for explaining an example of an information processing method in the information processing system shown in FIG. 11.

First, ion adsorption device 101 to which the ion adsorbent is attached is attached to branch pipe 11, the water flow is started to branch pipe 11 (step S1). At this time, after ion adsorption device 101 is attached to branch pipe 11, on-off valve 23, flow rate adjusting valve 25, three-way valve 28 and on-off valve 12 shown in FIG. 1 or FIG. 3 are opened, the water flow to the ion adsorbent is started. Thereafter, when a predetermined period has elapsed, or, when the accumulated value accumulated flow rate meter 26 shown in FIG. 1 or FIG. 3 is measured reaches a predetermined value, the water flow to branch pipe 11 is completed. As regards the end of the water flow to branch pipe 11, rather than the processing is directly caused by deleting that a predetermined period is passed or accumulated value has reached a predetermined value, these detections activates the notification process to that effect, by the person who has received the notification closes the valve, the flow of water to branch pipe 11 is intended to end. At this time, on-off valve 23, flow rate adjusting valve 25, three-way valve 28 and on-off valve 12 shown in FIG. 1 or FIG. 3 are closed. Here, ion adsorption device 101 has a timer, and measures the time from when the water flow to the ion adsorbent is started, and when a preset time has elapsed, notification unit 110 notifies that, it may be intended to complete the water flow to branch pipe 11. Further, when the accumulated value that accumulated flow rate meter has measured becomes a preset value, notification unit 110 notifies that, it may be intended to complete the flow of water to branch pipe 11. Notification that notification unit 110 performs is for the manager or the like of the system, and this person closes on-off valve 23, flow rate adjusting valve 25, three-way valve 28 and on-off valve 12, and may complete the water through by the notification. Notification unit 110 notifies on-off valve 23, flow rate adjusting valve 25, three-way valve 28 and on-off valve 12 of it, on-off valve 23, flow rate adjusting valve 25, three-way valve 28 and on-off valve 12 may close automatically to complete the water flow. Then, ion adsorption device 101 is removed from branch pipe 11 (Step S2). At this time, a new ion adsorption device 101 is attached to branch pipe 11. Further, the timer and the accumulated flow rate meter are reset each time that ion adsorption device 101 is attached to branch pipe 11 (replaced).

Thereafter, the information of the ion adsorbent that has been attached to the removed ion adsorption device 101 is provided to information processing apparatus 301 (step S3). The information provided is the period information of the ion adsorbent attached to ion adsorption device 101, the accumulated value measured by the accumulated flow rate meter, the adsorbent identification information of the ion adsorbent and the installation information of ion adsorption device 101 that has been attached. The method of providing these information may be such that ion adsorption device 101 transmits and provides this information to information processing apparatus 301, or may be provided via another medium. The timing at which the information of the ion adsorbent is provided to information processing apparatus 301 may be after step S1. Information provided in this case is information indicating the date and time when the water flow is started to branch pipe 11 after ion adsorption device 101 is attached to branch pipe 11. Then, the storage process is performed in information processing apparatus 301 (step S4). Note that the ion adsorbent that has been removed is stored at a predetermined place so that it can be identified using the adsorbent identification information.

Subsequently, when information processing apparatus 301 instructs quantitation apparatus 201 to perform a quantitative analysis (step S5), quantitation apparatus 201 performs the quantitative analysis (step S6). At this time, information processing apparatus 301 designates adsorbent identification information to direct quantitation apparatus 201 to carry out a quantitative analysis, and quantitation apparatus 201 performs quantitative analysis of ions adsorbed on the ion adsorbent to which the indicated adsorbent identification information is assigned. This method of instructing quantitative analysis may be one in which information indicating that information processing apparatus 301 requires quantitative analysis to quantitation apparatus 201 is transmitted and instructed, or may be provided via another medium. When the quantitative analysis is completed, quantitation apparatus 201 provides the result to the information processing apparatus 301 (Step S7). The method of providing the result of this quantitative analysis may be one in which quantitation apparatus 201 transmits and provides information indicating the result of the quantitative analysis to information processing apparatus 300, or may be one in which the quantitative analysis is provided via another medium. Then, information processing apparatus 301 performs output processing (step S8). Note that the ion adsorbent which has been subjected to the quantitative analysis is washed and stored so as to be able to be reused.

Figure 14:
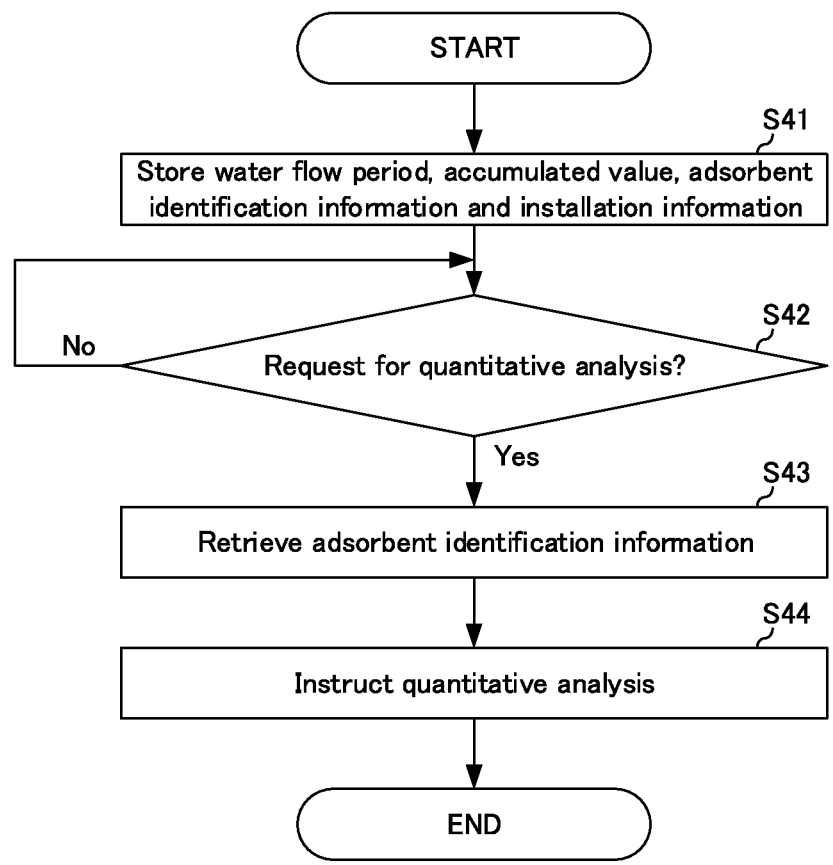
FIG. 14 is a flowchart for explaining an example of detailed processing of step S4 described with reference to the sequence diagram shown in FIG. 13.

FIG. 14 is a flowchart for explaining an example of detailed processing of the step S4 described with reference to the sequence diagram shown in FIG. 13. When information is provided from ion adsorption device 101 in step S3, database 321 stores the period information (water flow period) that is provided information, accumulated value, the adsorbent identification information and installation information in association each other (step S41). This association is stored in the form shown in FIGS. 8 and 9.

Thereafter, input unit 311 determines whether or not there is a request for quantitative analysis (Step S42). At this time, input unit 311 may determine that there is a request for quantitative analysis if the information that corresponds to the operation received from the outside or the information transmitted from another device connected to the outside includes the information to request quantitative analysis, the installation information and the date and time information. When there is a request for quantitative analysis, input unit 311 outputs the installation information and the date and time information among the input information to retrieval unit 331. Retrieval unit 331 retrieves the adsorbent identification information from database 321 based on the installation information and the date and time information output from input unit 311 (Step S43). Specifically, for example, retrieval unit 331 retrieves the adsorbent information from database 321 based on the installation information output from input unit 311, and, retrieves the adsorbent identification information associated with a period that includes the date and time information output from input unit 311 among the retrieved adsorbent information items from database 321. When the adsorbent identification information can be retrieved, retrieval unit 331 specifies the retrieved adsorbent identification information and instructs quantitation apparatus 201 to perform a quantitative analysis (Step S44).

Figure 15:
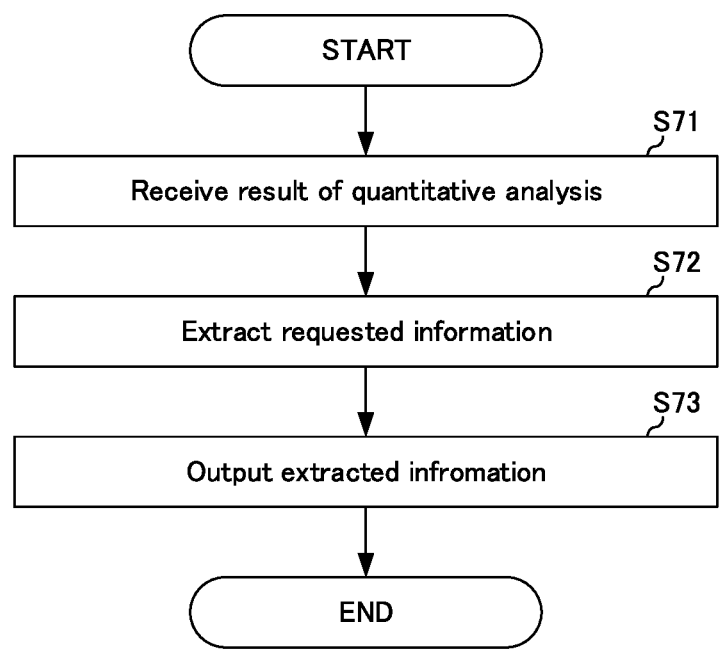
FIG. 15 is a flowchart for explaining an example of detailed processing of step S8 described with reference to the sequence diagram shown in FIG. 13.

FIG. 15 is a flowchart for explaining an example of detailed processing of the step S8 described with reference to the sequence diagram shown in FIG. 13. When input unit 311 receives the result of the quantitative analysis from quantitation apparatus 201 (Step S71), extraction unit 341 extracts the provided information that is the information that corresponds to the input information from the result of the quantitative analysis received by input unit 311 (Step S72). In some cases, the content of the quantitative analysis (e.g., the type of metal ion to be analyzed) is specified in the input information, and in this case, extraction unit 341 extracts the analysis content contained in the input information from the result of the quantitative analysis performed by quantitation apparatus 201. Subsequently, output unit 351 outputs the provided information extracted by extraction unit 341 (step S73). Note that quantitation apparatus 201 may calculate an impurity ion concentration in the water to be analyzed using the result of the quantitative analysis and the accumulated value measured by the accumulated flow rate meter, and input unit 311 may receive the impurity ion concentration in the water to be analyzed.

Thus, in the system for performing water quality management, the ion adsorption device ion adsorbent that is provided is exchanged at a predetermined timing, the ion adsorbent that is provided in the removed ion adsorption device is stored, among the stored ion adsorbent, the ion adsorbent of ion adsorption device attached to the specified installation location and period is retrieved quantitative analysis of the retrieved ion adsorbent is performed, and the result is output. Therefore, it is possible to recognize the process status of the water being analyzed at the specified location and date and time.

Although described above by allocating each function (processing) to each component, this assignment is not limited to those described above. In addition, as for the configuration of the component, the above-described form is merely an example, and is not limited thereto. In addition, the present invention can be applied to a system for controlling and managing a content amount of content of a metal in a liquid in addition to a system for performing water process.

The processing performed by the above-described information processing apparatus 300, 301 may be performed by logic circuits manufactured according to the purpose. Further, a computer program (hereinafter, referred to as a program) describing the processing contents as a procedure may be recorded in a readable recording medium by information processing apparatus 300,301, and a program recorded in the recording medium may be read into information processing apparatus 300,301 and executed. The recording medium readable by information processing apparatus 300,301 includes a floppy (registered trademark) disk, a magnetic-optical disk, a DVD (Digital Versatile Disc), a CD (Compact Disc), a Blu-ray (registered trademark) Disc, a relocatable recording medium such as a USB (Universal Serial Bus) memory, a ROM (Read Only Memory) built in information processing apparatus 300,301, a memory such as a RAM (Random Access Memory), an HDD (Hard Disc Drive), and the like. The program recorded on the recording medium is read by a CPU provided in information processing apparatus 300,301, and the same processing as described above is performed under the control of the CPU. Here, the CPU operates as a computer that executes a program read from a recording medium in which a program is recorded.

REFERENCE SIGNS LIST

10 Ultrapure water supply pipe
11 Branch pipe
12,23 On-off valve
20,100,101 Ion adsorption device
21 Fitting
22 Internal pipe
24 Ion adsorbent
25 Flow rate adjusting valve
26 Accumulated flow rate meter
27 Discharge pipe
28 Three-way valve
110 Notification unit
200,201 Quantitation apparatus
300,301 Information processing apparatus
310,311 Input unit
320,321 Database
330,331 Retrieval unit
341 Extraction unit
350,351 Output unit

The invention claimed is:

1. A water quality management method, comprising:
connecting an ion adsorption device in which an ion adsorbent and an accumulated flow rate meter are provided to a branch pipe through which water being analyzed flows,
passing the water being analyzed from the branch pipe to the ion adsorbent for a predetermined period of time with respect to the ion adsorption device, and adsorbing ions contained in the water being analyzed to an ion adsorbent sample, and
providing the accumulated flow rate meter in the ion adsorption device on the downstream side of the flow direction of water being analyzed of the ion adsorbent.

2. The water quality management method according to claim 1, further comprising:
processing for removing the ion adsorption device from the branch pipe in a state of closing both ends of the ion adsorbent sample after the end of the predetermined period,
wherein both ends of the ion adsorbent sample are kept closed until analysis of the ion adsorbent sample is performed.

3. The water quality management method according to claim 1, further comprising:
processing for obtaining the ion adsorbent sample continuously over a plurality of periods by repeating the flow of the water being analyzed to a new ion adsorption device by connecting the new ion adsorption device to the branch pipe by removing the ion adsorption device from the branch pipe.

4. The water quality management method according to claim 3, further comprising:
processing for recording a water flow period for the ion adsorbent sample for each of the plurality of ion adsorbent samples.

5. The water quality management method according to claim 4, further comprising:
performing a quantitative analysis of at least a portion of the water used in a manufacturing process of a product, wherein the water being subjected to the quantitative analysis is one or more water samples that were collected during a water flow period of the manufacturing process in which the product was manufactured.

6. The water quality management method according to claim 5, wherein
the one or more water samples being analyzed are each associated with period information that is recorded and identifies the water flow period by at least a day when the water flow is started to the ion adsorption device and a day when the water flow is completed, and
an adsorbent identification information is assigned and is recorded in association with the period information of the water flow period from which the analyzed one or more water samples were collected and the quantitative analysis.

7. The water quality management method according to claim 1,
wherein the branch pipe is a pipe for supplying ultrapure water to a point of use by branching from an ultrapure water producing apparatus or a pipe branching from the pipe.

8. An ion adsorption device which is detachably connected to a branch pipe through which a water being analyzed flows, comprising:
an ion adsorbent that is provided removably and that adsorbs ions of the water being analyzed through which the water being analyzed is passed, and
an accumulated flow rate meter that is provided on a downstream side of a flow direction of the water being analyzed, of the ion adsorbent, and that measures the accumulated value of the water flow rate of the ion adsorbent.

9. The ion adsorption device according to claim 8, further comprising:
a first valve that is disposed between the ion adsorbent and the accumulated flow rate meter, that is configured to regulate and shut off the water being analyzed, and that is capable of adjusting the flow rate of the water being analyzed.

10. The ion adsorption apparatus according to claim 8, further comprising:
a second valve that is configured to regulate and shut off the water being analyzed at the upstream side of the flow direction of the water being analyzed, of the ion adsorbent.

11. An information processing apparatus, comprising:
an input unit that inputs input information into the information processing apparatus,
a database that stores period information indicating a time when an ion adsorbent for adsorbing ions of the water being analyzed through which the water being analyzed is passed is attached to a branch pipe through which the water being analyzed is passed and an adsorbent identification information assigned to the ion adsorbent specific in association with each other, a retrieval unit that retrieves a period including the date and time indicated by the date and time information included in the input information input by the input unit from the database, and retrieves the adsorbent identification information associated with the retrieved period from the database, and an output unit that outputs the adsorbent identification information retrieved by the retrieval unit so that a quantitation apparatus performs quantitative analysis on the ion adsorbent to which the adsorbent identification information retrieved by the retrieval unit has been assigned.

12. The information processing apparatus according to claim 11, wherein the input unit, when a predetermined period of time has elapsed since the ion adsorbent was attached to the branch pipe, or when an accumulated value measured by an accumulated flow rate meter after the ion adsorbent was attached to the branch pipe becomes a predetermined value, inputs the information for instructing the retrieval of the ion adsorbent sample.

13. An information processing system, comprising:
an ion adsorption device,
a quantitation apparatus, and
an information processing apparatus,
wherein the ion adsorption device, comprises:
an ion adsorbent that is removably provided in a branch pipe in which the water being analyzed flows, and that adsorbs ions of the water being analyzed through which the water being analyzed is passed, and
an accumulated flow rate meter that is provided on the downstream side of the flow direction of the water being analyzed of the ion adsorbent, and that measures the accumulated value of the water flow rate of the ion adsorbent, wherein the information processing apparatus, comprises:
an input unit that inputs input information into the information processing apparatus,
a database that stores period information indicating the time when the ion adsorbent has been attached to the branch pipe and an adsorbent identification information assigned to the ion adsorbent specific in association with each other,
a retrieval unit that retrieves the adsorbent identification information from the database based on the date and time information included in the input information input by the input unit, and
an output unit that outputs the adsorbent identification information retrieved by the retrieval unit, wherein the quantitation apparatus performs quantitative analysis on the ion adsorbent to which the adsorbent identification information output by the output unit is assigned, wherein the output unit outputs provided information based on the results of quantitative analysis performed by the quantitation apparatus.

14. The information processing system according to claim 13, further comprising:
an extraction unit that extracts the provided information which is information corresponding to the input information from the result of the quantitative analysis performed by the quantitation apparatus with respect to the ion adsorbent to which the adsorbent identification information retrieved by the retrieval unit is assigned,
wherein the output unit outputs the provided information extracted by the extraction unit.

15. The information processing system according to claim 13, further comprising:
a notification unit that performs a predetermined notification when a predetermined period has elapsed since the ion adsorbent was attached to the branch pipe, or when the accumulated value measured by the accumulated flow rate meter after the ion adsorbent was attached to the branch pipe becomes a predetermined value.

* * * * *